United States Patent
Cohen et al.

(10) Patent No.: US 10,545,144 B2
(45) Date of Patent: Jan. 28, 2020

(54) DIAGNOSIS OF SYSTEMIC LUPUS ERYTHEMATOSUS USING OLIGONUCLEOTIDES ANTIGENS

(71) Applicant: YEDA RESEARCH AND DEVELOPMENT CO. LTD., Rehovot (IL)

(72) Inventors: Irun R. Cohen, Rehovot (IL); Eytan Domany, Rehovot (IL); Noam Shental, Rehovot (IL); Ittai Fattal, Rehovot (IL)

(73) Assignee: YEDA RESEARCH AND DEVELOPMENT CO., LTD., Rehovot (IL)

( * ) Notice: Subject to any disclaimer, the term of this patent is extended or adjusted under 35 U.S.C. 154(b) by 295 days.

(21) Appl. No.: 15/108,889

(22) PCT Filed: Dec. 31, 2014

(86) PCT No.: PCT/IL2014/051142
§ 371 (c)(1),
(2) Date: Jun. 29, 2016

(87) PCT Pub. No.: WO2015/101988
PCT Pub. Date: Jul. 9, 2015

(65) Prior Publication Data
US 2017/0016895 A1    Jan. 19, 2017

Related U.S. Application Data

(60) Provisional application No. 61/922,114, filed on Dec. 31, 2013.

(51) Int. Cl.
*G01N 33/564* (2006.01)
*C12Q 1/6883* (2018.01)

(52) U.S. Cl.
CPC ......... *G01N 33/564* (2013.01); *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 3,849,550 A | 11/1974 | Teitelbaum |
| 4,208,479 A | 6/1980 | Zuk et al. |
| 5,114,844 A | 5/1992 | Cohen |
| 5,326,357 A | 7/1994 | Kandel |
| 5,578,303 A | 11/1996 | Cohen |
| 5,671,848 A | 9/1997 | Cohen |
| 5,700,641 A | 12/1997 | Salonen |
| 5,763,158 A | 6/1998 | Bohannon |
| 5,780,034 A | 7/1998 | Cohen |
| 5,800,808 A | 9/1998 | Konfino |
| 5,858,804 A | 1/1999 | Zanzucchi |
| 5,981,700 A | 11/1999 | Rabin |
| 6,048,898 A | 4/2000 | Konfino |
| 6,054,430 A | 4/2000 | Konfino |
| 7,276,341 B2 | 10/2007 | Harley |
| 7,476,514 B2 | 1/2009 | Britz |
| 8,010,298 B2 | 8/2011 | Cohen |
| 2003/0003516 A1 | 1/2003 | Robinson |
| 2003/0087848 A1 | 5/2003 | Bratzler |
| 2004/0014069 A1 | 1/2004 | Cohen |
| 2005/0260770 A1 | 11/2005 | Cohen |
| 2007/0141627 A1 | 6/2007 | Behrens |
| 2008/0254482 A1 | 10/2008 | Mattoon |
| 2008/0293660 A1 | 11/2008 | Coutts |
| 2009/0246195 A1 | 10/2009 | Tedder |
| 2009/0258790 A1 | 10/2009 | Cohen |
| 2010/0160415 A1 | 6/2010 | Solvason |
| 2011/0312016 A1 | 12/2011 | Pankewycz |
| 2012/0077689 A1 | 3/2012 | Sarwal |
| 2012/0122720 A1 | 5/2012 | Cohen |
| 2013/0183686 A1 | 7/2013 | Pankewycz |

FOREIGN PATENT DOCUMENTS

| | | |
|---|---|---|
| CN | 1954216 | 4/2007 |
| CN | 101329341 | 12/2008 |
| EP | 0417271 | 3/1991 |
| EP | 1630557 | 3/2006 |
| EP | 2336769 | 6/2011 |
| GB | 2460717 | 12/2009 |
| JP | 2005509127 | 4/2005 |
| WO | 9939210 | 8/1999 |
| WO | 0182960 | 11/2001 |
| WO | 0208755 | 1/2002 |
| WO | 2008082730 A2 | 7/2008 |
| WO | 2010055510 | 5/2010 |
| WO | 2010128506 | 11/2010 |

(Continued)

OTHER PUBLICATIONS

Cavallo et al, Autoimmune Diseases, Article 814048, pp. 1-10 (2012).*
Abulafia-Lapid et al., (1999) T cell proliferative responses of type 1 diabetes patients and healthy individuals to human hsp60 and its peptides. J Autoimmun 12(2): 121-9.
Abulafia-Lapid et al., (2003) T cells and autoantibodies to human HSP70 in type 1 diabetes in children. J Autoimmun 20(4): 313-21.
Abu-Shakra et al., (1995) Mortality studies in systemic lupus erythematosus. Results from a single center. I. Causes of death. Tthe Journal of Rheumatology, 22(7), 1259-1264.
Alon et al., (1999) Broad patterns of gene expression revealed by clustering analysis of tumor and normal colon tissues probed by oligonucleotide arrays. Proc Natl Acad Sci U S A 96(12): 6745-50, p. 6749 r-h Col.

(Continued)

*Primary Examiner* — James Martinell
(74) *Attorney, Agent, or Firm* — J.A. Lindeman & Co., PLLC; Jeffrey Lindeman; Sulay Jhaveri

(57) ABSTRACT

Methods and kits for diagnosing systemic lupus erythematosus (SLE) in a subject are provided. Particularly, the present invention relates to specific oligonucleotide antibody reactivities useful in diagnosing SLE in a subject.

1 Claim, 11 Drawing Sheets
Specification includes a Sequence Listing.

(56) References Cited

FOREIGN PATENT DOCUMENTS

| WO | 2011099012 | | 8/2011 |
|---|---|---|---|
| WO | 2012052994 | | 4/2012 |
| WO | 2013022995 | A2 | 2/2013 |
| WO | 2014091490 | | 6/2014 |
| WO | 2014195730 | | 12/2014 |
| WO | 2015101987 | A1 | 7/2015 |
| WO | 2015/101988 | A1 | 9/2015 |

OTHER PUBLICATIONS

Barzilai et al., (2007) Epstein-Barr virus and cytomegalovirus in autoimmune diseases: are they truly notorious? A preliminary report. Ann N Y Acad Sci 1108(1): 567-577.
Batstra et al., (2001) Prediction and diagnosis of type 1 diabetes using beta-cell autoantibodies. Clin Lab 47(9-10): 497-507, abstract.
Cahill (2000) Protein arrays: a high-throughput solution for proteomics research? Trends in Biotechnology 18: 47-51.
Chagnon et al., (2006) Identification and characterization of an Xp22.33;Yp11.2 translocation causing a triplication of several genes of the pseudoautosomal region 1 in an XX male patient with severe systemic lupus erythematosus. Arthritis Rheum 54(4): 1270-8.
Cohen, (2007) Real and artificial immune systems: computing the state of the body. Nature Reviews Immunology, 7(7) : 569-574.
Diaz-Quijada & Wayner, (2004) A simple approach to micropatterning and surface modification of poly (dimethylsiloxane). Langmuir, 20(22), 9607-9611.
Domany (1999) Superparamagnetic clustering of data—The definitive solution of an ill-posed problem. Physica A: Statistical Mechanics and its Applications 263(1-4): 158-169, pp. 166-168.
Eisen et al., (1998) Cluster analysis and display of genome-wide expression patterns. Proc Natl Acad Sci U S A 95(25): 14863-8.
Elizur G., Thesis, Antigen Chip: Development and Analysis; An Application to Autoimmune Diseases, The Weizmann Institute of Science, Israel, Jan. 2004, 1-78.
Esen et al., (2012) Serologic response to Epstein-Barr virus antigens in patients with systemic lupus erythematosus: a controlled study. Rheumatol Int 32(1): 79-83.
Faaber et al.,(1984) Cross-reactivity of anti-DNA antibodies with proteoglycans. Clin Exp Immunol 55(3): 502-508.
Fattal et al., (2010) An antibody profile of systemic lupus erythematosus detected by antigen microarray. Immunology, 130(3), 337-343.
Fattal et al., (2015) Guanine polynucleotides are self-antigens for human natural autoantibodies and are significantly reduced in the human genome. Immunology, 146(3), 401-410.
Ferreira et al., (1997) Instability of natural antibody repertoires in systemic lupus erythematosus patients, revealed by multiparametric analysis of serum antibody reactivities. Scand J Immunol 45(3): 331-41.
Fraley and Raftery (1998) How many clusters? Which clustering method? Answers via model-based cluster analysis. Technical report No. 329, Department of Statistics, University of Washington, Seattle, WA, P.I, 1-19.
Getz et al., (2000) Coupled two-way clustering analysis of gene microarray data. Proc Natl Acad Sci U S A 97(22): 12079-84.
Golub et al., (1999) Molecular classification of cancer: class discovery and class prediction by gene expression monitoring. Science 286(5439): 531-7.
Grus et al., (1998) Diagnostic classification of autoantibody repertoires in endocrine ophthalmopathy using an artificial neural network. Ocular immunology and inflammation, 6(1), 43-50.
Hanly et al., (2010) Measurement of autoantibodies using multiplex methodology in patients with systemic lupus erythematosus. J Immunol Methods 352(1-2): 147-152.
Harley and James (2006) Epstein-Barr virus infection induces lupus autoimmunity. Bull NYU Hosp Jt Dis 64(1-2): 45-50.

Herkel et al., (2001) Autoimmunity to the p53 protein is a feature of systemic lupus erythematosus (SLE) related to anti-DNA antibodies. J Autoimmun 17(1): 63-9.
Herkel et al., "Monoclonal antibody to a DNA-binding domain of p53 mimics charge structure of DNA: anti-idiotypes to the anti-p53 antibody are anti-DNA", Eur. J. Immunol., 2004, vol. 34, pp. 3623-3632.
Hochberg (1997) Updating the American College of Rheumatology revised criteria for the classification of systemic lupus erythematosus. Arthritis Rheum 40: 1725.
Invitrogen, HuProtV2 array, 2007. 2 pages.
Isenberg et al., (1986) The relationship of anti-DNA antibody idiotypes and anti-cardiolipin antibodies to disease activity in systemic lupus erythematosus. Medicine (Baltimore) 65(1): 46-55.
Ito et al., (1992) Cell proliferation in childhood acute leukemia. Comparison of Ki-67 and proliferating cell nuclear antigen immunocytochemical and DNA flow cytometric analysis. Cancer 69(8): 2176-82.
James & Robertson, (2012) Lupus and epstein-barr. Current opinion in rheumatology, 24(4), 383-388.
James et al., (1997) An increased prevalence of Epstein-Barr virus infection in young patients suggests a possible etiology for systemic lupus erythematosus. J Clin Invest 100(12): 3019-3026.
Joos et al., (2000) A microarray enzyme-linked immunosorbent assay for autoimmune diagnostics. Electrophoresis 21(13): 2641-50.
Kang et al., (2004) Defective control of latent Epstein-Barr virus infection in systemic lupus erythematosus. J Immunol 172(2): 1287-94.
Kanter et al., (2006) Lipid microarrays identify key mediators of autoimmune brain inflammation. Nature medicine, 12(1), 138-143.
Khoshnoodi et al., (2008) Mammalian collagen IV. Microsc Res Tech 71(5): 357-370.
Kobayashi et al., (2013) Oligodeoxynucleotides expressing polyguanosine motifs promote antitumor activity through the upregulation of IL-2. The Journal of Immunology, 190(4), 1882-1889.
Koffler et al., (1971) Antibodies to polynucleotides in human sera: antigenic specificity and relation to disease. Journal of Experimental Medicine, 134(1), 294-312.
Könen-Waisman et al., (1995) Self and foreign 60-kilodalton heat shock protein T cell epitope peptides serve as immunogenic carriers for a T cell-independent sugar antigen. J Immunol 154(11): 5977-85.
Kupinski & Anastasio, (1999) Multiobjective genetic optimization of diagnostic classifiers with implications for generating receiver operating characteristic curves. IEEE Transactions on Medical Imaging, 18(8), 675-685.
Lenert, (2010) Nucleic acid sensing receptors in systemic lupus erythematosus: development of novel DNA-and/or RNA-like analogues for treating lupus. Clinical & Experimental Immunology, 161(2), 208-222.
Li et al., (2007) Protein array autoantibody profiles for insights into systemic lupus erythematosus and incomplete lupus syndromes. Clin Exp Immunol 147(1): 60-70.
Liang et al., (1989) Reliability and validity of six systems for the clinical assessment of disease activity in systemic lupus erythematosus. Arthritis & Rheumatology, 32(9), 1107-1118.
Lieberman and DiLorenzo (2003) A comprehensive guide to antibody and T-cell responses in type 1 diabetes. Tissue Antigens 62(5): 359-77.
Lossos et al., (1998) Anticardiolipin antibodies in acute myeloid leukemia: prevalence and clinical significance. Am J Hematol 57(2): 139-43.
Love, and Santoro (1990) Antiphospholipid antibodies: anticardiolipin and the lupus anticoagulant in systemic lupus erythematosus (SLE) and in non-SLE disorders. Prevalence and clinical significance. Ann Intern Med 112(9): 682-698.
Manolova et al., (2002) Predominance of IgG1 and IgG3 subclasses of autoantibodies to neutrophil cytoplasmic antigens in patients with systemic lupus erythematosus. Rheumatol Int 21(6): 227-233.
Masi (1980) Preliminary criteria for the classification of systemic sclerosis (scleroderma). Arthritis & Rheumatism 23(5): 581-590.

(56) References Cited

OTHER PUBLICATIONS

Mattoon et al., (2007) Biomarker Discovery: Immune Response Profiling on ProtoArray® Human Protein Microarrays. 1-6.
Merbl et al., (2007) Newborn humans manifest autoantibodies to defined self molecules detected by antigen microarray informatics. Journal of Clinical Investigation, 117(3), 712-718.
Mor et al., (1996) IL-2 and TNF receptors as targets of regulatory T-T interactions: isolation and characterization of cytokine receptor-reactive T cell lines in the Lewis rat. J Immunol 157(11): 4855-61.
Moreland et al., (1991) Collagen autoantibodies in patients with vasculitis and systemic lupus erythematosus. Clin Immunol Immunopathol 60(3): 412-418.
Nahon et al., (1982) Anti-poly (G)• poly (C) antibodies in the serum of patients with systemic lupus erythematosus. Clinical immunology and immunopathology, 22(3), 349-362.
Niller et al., (2008) Regulation and dysregulation of Epstein-Barr virus latency: implications for the development of autoimmune diseases. Autoimmonity 41(4): 298-328191.
Oliva et al., (1998) Automated classification of antibody complementarity determining region 3 of the heavy chain (H3) loops into canonical forms and its application to protein structure prediction. J Mol Biol 279(5): 1193-210, pp. 1193-1194.
Pal et al., (2000) Identification and purification of cytolytic antibodies directed against O-acetylated sialic acid in childhood acute lymphoblastic leukemia. Glycobiology 10(6): 539-49.
Park, (2001) Primary structures and chain dominance of anti-DNA antibodies. Molecules & Cells (Springer Science & Business Media BV), 11(1).
Pavlovic et al., (2010) Pathogenic and Epiphenomenal Anti-DNA Antibodies in SLE Autoimmune diseases, 462841.
Peng et al., (2005) Toll-like receptor 8-mediated reversal of CD4+ regulatory T cell function. Science, 309(5739), 1380-1384.
Petri et al., (1991) Morbidity of systemic lupus erythematosus: role of race and socioeconomic status. The American journal of medicine, 91(4), 345-353.
Petri et al., (2012) Derivation and validation of the Systemic Lupus International Collaborating Clinics classification criteria for systemic lupus erythematosus. Arthritis & Rheumatology, 64(8), 2677-2686.
Quintana & Cohen, (2001) Autoantibody patterns in diabetes-prone NOD mice and in standard C57BL/6 mice. Journal of autoimmunity, 17(3), 191-197.
Quintana et al., (2003) Cluster analysis of human autoantibody reactivities in health and in type 1 diabetes mellitus: a bioinformatic approach to immune complexity. Journal of autoimmunity, 21(1), 65-75.
Quintana et al., (2004) Functional immunomics: microarray analysis of IgG autoantibody repertoires predicts the future response of mice to induced diabetes. Proceedings of the National Academy of Sciences, 101(suppl 2), 14615-14621.
Quintana et al., (2006) Antigen-chip technology for accessing global information about the state of the body. Lupus, 15(7), 428-430.
Quintana et al., (2008) Antigen microarrays identify unique serum autoantibody signatures in clinical and pathologic subtypes of multiple sclerosis. Proc Natl Acad Sci USA 105(48): 18889-18894.
Robinson et al., (2002) Autoantigen microarrays for multiplex characterization of autoantibody responses. Nature medicine, 8(3), 295-301.
Robinson et al., (2003) Protein microarrays guide tolerizing DNA vaccine treatment of autoimmune encephalomyelitis. Nature biotechnology, 21(9), 1033-1039.
Sen and Isenberg (2003) Antineutrophil cytoplasmic autoantibodies in systemic lupus erythematosus. Lupus 12(9): 651-658.
Sherer et al., (2004) Autoantibody explosion in systemic lupus erythematosus: more than 100 different antibodies found in SLE patients. In Seminars in arthritis and rheumatism (vol. 34, No. 2, pp. 501-537). WB Saunders.
Sternbaek et al., (2017) Efficient evaluation of humoral immune responses by the use of serum pools. Journal of Immunological Methods, 443, 1-8.
Tan et al., (1982) The 1982 revised criteria for the classification of systemic lupus erythematosus. Arthritis & Rheumatology, 25(11), 1271-1277.
Toussirot and Roudier (2008) Epstein-Barr virus in autoimmune diseases. Best Pract Res Clin Rheumatol 22(5): 883-96.
Vincenti et al., (2010) A phase III study of belatacept-based immunosuppression regimens versus cyclosporine in renal transplant recipients (BENEFIT study). American Journal of Transplantation, 10(3), 535-546.
Wold et al., (1968) Deoxyribonucleic acid antibody: A method to detect its primary interaction with deoxyribonucleic acid. Science 161(3843): 806-807.
Zagorodniuk et al., (2005) A comparison of anti-desmoglein antibodies and indirect immunofluorescence in the serodiagnosis of pemphigus vulgaris. International journal of dermatology 44(7): 541-544.
Zhen et al., (2005) Identification of autoantibody clusters that best predict lupus disease activity using glomerular proteome arrays. J Clin Invest 115(12): 3428-3439.
Hawro et al., (2015) Serum neuron specific enolase—a novel indicator for neuropsychiatric systemic lupus erythematosus? Lupus 24(14): 1492-1497.
Ronnefarth V., Dissertation, The Role of Nucleosome-Induced Neutrophil Activation in Systemic Lupus Erythmatosus, The Eberhard Karls University of Tubingen, Germany 2007, 1-78.
Swissa et al., (1990) Autoantibodies in neoplasia. An unresolved enigma. Cancer 65(11): 2554-2558.
Swissa et al., (1991) Determination of autoantibodies in patients with familial Mediterranean fever and their first degree relatives. J Rheumatol 18(4): 606-608.
To and Midwood (2011) Plasma and cellular fibronectin: distinct and independent functions during tissue repair. Fibrogenesis Tissue Repair 4: 21; 17 pages.

\* cited by examiner

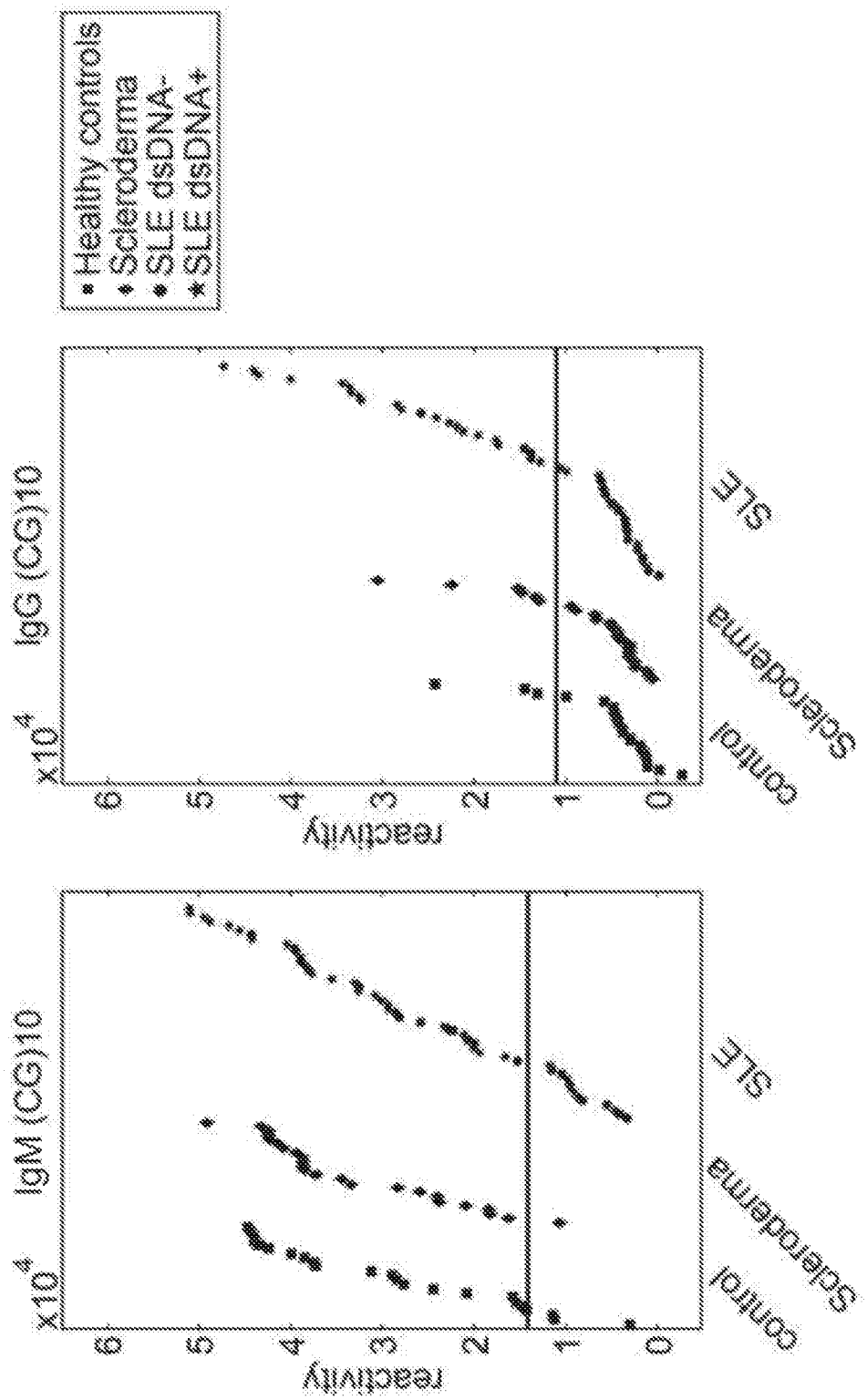

| Antigen (IgG) SEQ ID NO: | fit AUC | AUC BootstrapEst Estimate | Lower95 %CI | Uper95 %CI | pval |
|---|---|---|---|---|---|
| 5 | 0.902 | 0.902 | 0.831 | 0.972 | 1.07E-18 |
| 28 | 0.861 | 0.865 | 0.786 | 0.945 | 4.81E-15 |
| 42 | 0.857 | 0.854 | 0.763 | 0.944 | 9.49E-15 |
| 3 | 0.850 | 0.852 | 0.775 | 0.930 | 9.87E-14 |
| 8 | 0.844 | 0.841 | 0.754 | 0.927 | 8.00E-14 |
| 7 | 0.838 | 0.838 | 0.753 | 0.923 | 2.38E-11 |
| 17 | 0.821 | 0.812 | 0.712 | 0.913 | 2.39E-12 |
| 1 | 0.819 | 0.820 | 0.722 | 0.919 | 2.81E-12 |
| 66 | 0.792 | 0.787 | 0.689 | 0.885 | 5.43E-09 |
| 10 | 0.786 | 0.787 | 0.685 | 0.889 | 1.34E-10 |
| 34 | 0.774 | 0.777 | 0.671 | 0.884 | 1.55E-09 |
| 65 | 0.761 | 0.755 | 0.642 | 0.867 | 5.16E-09 |
| 44 | 0.761 | 0.765 | 0.674 | 0.860 | 8.10E-09 |
| 67 | 0.757 | 0.759 | 0.636 | 0.822 | 4.99E-07 |
| 22 | 0.756 | 0.762 | 0.655 | 0.869 | 1.87E-08 |
| 43 | 0.754 | 0.753 | 0.655 | 0.852 | 1.03E-08 |
| 36 | 0.743 | 0.741 | 0.647 | 0.836 | 3.15E-08 |
| 18 | 0.688 | 0.689 | 0.568 | 0.810 | 1.06E-05 |
| 45 | 0.682 | 0.672 | 0.565 | 0.780 | 3.90E-05 |
| 38 | 0.655 | 0.664 | 0.584 | 0.794 | 0.000438 |
| 15 | 0.649 | 0.652 | 0.523 | 0.781 | 0.001622 |
| 25 | 0.621 | 0.624 | 0.498 | 0.751 | 0.003183 |
| 41 | 0.501 | 0.469 | 0.361 | 0.777 | 0.72906 |

FIGURE 7AI

| | Assume cutpoint with PPV ≥0.9 and Pravalence of 10% |||||||||
|---|---|---|---|---|---|---|---|---|
| Antigen (IgG) | Sensitivity ||| Specificity ||| Accuracy |||
| SEQ ID NO: | Estimate | Lower95 %CI | Uper95 %CI | Estimate | Lower95 %CI | Uper95 %CI | Estimate | Lower95 %CI | Uper95 %CI |
|---|---|---|---|---|---|---|---|---|---|
| 5 | 0.767 | 0.600 | 0.934 | 0.869 | 0.749 | 0.989 | 0.819 | 0.732 | 0.905 |
| 28 | 0.682 | 0.471 | 0.894 | 0.856 | 0.696 | 1.016 | 0.769 | 0.676 | 0.862 |
| 42 | 0.680 | 0.476 | 0.884 | 0.822 | 0.693 | 0.950 | 0.750 | 0.660 | 0.840 |
| 3 | 0.659 | 0.450 | 0.867 | 0.830 | 0.651 | 1.008 | 0.743 | 0.646 | 0.841 |
| 8 | 0.663 | 0.445 | 0.881 | 0.814 | 0.633 | 0.995 | 0.738 | 0.642 | 0.835 |
| 7 | 0.656 | 0.455 | 0.856 | 0.828 | 0.658 | 0.997 | 0.741 | 0.657 | 0.824 |
| 17 | 0.749 | 0.565 | 0.934 | 0.769 | 0.546 | 0.993 | 0.756 | 0.631 | 0.880 |
| 1 | 0.657 | 0.443 | 0.871 | 0.798 | 0.617 | 0.979 | 0.725 | 0.618 | 0.832 |
| 66 | 0.672 | 0.466 | 0.879 | 0.740 | 0.571 | 0.910 | 0.705 | 0.618 | 0.792 |
| 10 | 0.627 | 0.464 | 0.790 | 0.749 | 0.534 | 0.965 | 0.688 | 0.580 | 0.795 |
| 34 | 0.650 | 0.434 | 0.865 | 0.747 | 0.551 | 0.943 | 0.696 | 0.597 | 0.795 |
| 65 | 0.619 | 0.428 | 0.810 | 0.727 | 0.511 | 0.944 | 0.671 | 0.557 | 0.785 |
| 44 | 0.654 | 0.441 | 0.867 | 0.727 | 0.512 | 0.941 | 0.687 | 0.596 | 0.777 |
| 67 | 0.652 | 0.429 | 0.874 | 0.751 | 0.488 | 1.014 | 0.698 | 0.575 | 0.280 |
| 22 | 0.609 | 0.411 | 0.807 | 0.769 | 0.566 | 0.972 | 0.687 | 0.583 | 0.791 |
| 43 | 0.620 | 0.438 | 0.802 | 0.745 | 0.528 | 0.962 | 0.680 | 0.575 | 0.785 |
| 36 | 0.606 | 0.399 | 0.813 | 0.714 | 0.510 | 0.926 | 0.657 | 0.563 | 0.751 |
| 18 | 0.573 | 0.328 | 0.818 | 0.662 | 0.386 | 0.939 | 0.610 | 0.497 | 0.724 |
| 45 | 0.585 | 0.296 | 0.874 | 0.628 | 0.419 | 0.838 | 0.601 | 0.493 | 0.710 |
| 38 | 0.517 | 0.234 | 0.800 | 0.662 | 0.367 | 0.956 | 0.589 | 0.481 | 0.696 |
| 15 | 0.492 | 0.248 | 0.736 | 0.670 | 0.446 | 0.894 | 0.580 | 0.483 | 0.678 |
| 25 | 0.517 | 0.217 | 0.816 | 0.679 | 0.400 | 0.958 | 0.592 | 0.470 | 0.715 |
| 41 | 0.417 | -0.738 | 1.572 | 0.557 | -0.670 | 1.785 | 0.408 | 0.270 | 0.547 |

FIGURE 7AII

| Antigen (IgM) | AUC | BootstrapEst | | | |
|---|---|---|---|---|---|
| SEQ ID NO: | fit AUC | Estimate | Lower95 %CI | Uper95 %CI | pval |
| 44 | 0.595 | 0.593 | 0.450 | 0.736 | 0.030192 |
| 38 | 0.588 | 0.568 | 0.413 | 0.723 | 0.054927 |
| 5 | 0.588 | 0.571 | 0.373 | 0.770 | 0.05872 |
| 3 | 0.584 | 0.587 | 0.469 | 0.704 | 0.020982 |
| 42 | 0.584 | 0.569 | 0.432 | 0.705 | 0.074165 |
| 34 | 0.580 | 0.580 | 0.443 | 0.717 | 0.052334 |
| 65 | 0.575 | 0.563 | 0.415 | 0.711 | 0.066193 |
| 67 | 0.568 | 0.540 | 0.369 | 0.711 | 0.151489 |
| 10 | 0.564 | 0.559 | 0.432 | 0.686 | 0.151909 |
| 66 | 0.563 | 0.547 | 0.400 | 0.695 | 0.065437 |
| 17 | 0.562 | 0.536 | 0.377 | 0.696 | 0.187019 |
| 22 | 0.547 | 0.512 | 0.360 | 0.664 | 0.300825 |
| 8 | 0.543 | 0.513 | 0.378 | 0.648 | 0.214836 |
| 45 | 0.541 | 0.512 | 0.365 | 0.660 | 0.403384 |
| 7 | 0.538 | 0.509 | 0.379 | 0.639 | 0.257237 |
| 28 | 0.537 | 0.511 | 0.359 | 0.663 | 0.155343 |
| 36 | 0.535 | 0.488 | 0.324 | 0.651 | 0.597499 |
| 25 | 0.531 | 0.495 | 0.347 | 0.643 | 0.45527 |
| 43 | 0.531 | 0.470 | 0.322 | 0.619 | 0.449503 |
| 41 | 0.525 | 0.472 | 0.328 | 0.616 | 0.603059 |
| 15 | 0.452 | 0.505 | 0.336 | 0.675 | 0.345767 |

FIGURE 7BI

| Antigen (IgM) SEQ ID NO: | Assume cutpoint with PPV 0>9 and Pravalence of 10% | | | | | | | |
|---|---|---|---|---|---|---|---|---|
| | Sensitivity | | | Specificity | | | Accuracy | |
| | Estimate | Lower95 %CI | Uper95 %CI | Estimate | Lower95 %CI | Uper95 %CI | Estimate | Lower95 %CI | Uper95 %CI |
| 44 | 0.548 | 0.184 | 0.912 | 0.577 | 0.180 | 0.974 | 0.549 | 0.442 | 0.655 |
| 38 | 0.523 | -0.015 | 1.060 | 0.554 | 0.066 | 1.042 | 0.522 | 0.414 | 0.630 |
| 5 | 0.575 | -0.052 | 1.201 | 0.449 | -0.062 | 0.961 | 0.460 | 0.205 | 0.715 |
| 3 | 0.498 | 0.160 | 0.836 | 0.594 | 0.223 | 0.965 | 0.538 | 0.426 | 0.651 |
| 42 | 0.466 | 0.086 | 0.846 | 0.628 | 0.289 | 0.966 | 0.544 | 0.431 | 0.657 |
| 34 | 0.484 | 0.037 | 0.931 | 0.577 | 0.115 | 1.039 | 0.519 | 0.393 | 0.646 |
| 65 | 0.488 | 0.061 | 0.915 | 0.560 | 0.115 | 1.006 | 0.511 | 0.393 | 0.630 |
| 67 | 0.529 | 0.434 | 0.624 | 0.468 | 0.336 | 0.600 | 0.499 | 0.454 | 0.543 |
| 10 | 0.477 | 0.065 | 0.889 | 0.470 | 0.114 | 0.872 | 0.477 | 0.427 | 0.527 |
| 66 | 0.521 | 0.132 | 0.909 | 0.492 | 0.107 | 0.876 | 0.505 | 0.456 | 0.554 |
| 17 | 0.440 | -0.177 | 1.056 | 0.576 | -0.004 | 1.156 | 0.488 | 0.377 | 0.600 |
| 22 | 0.496 | 0.042 | 0.949 | 0.503 | 0.113 | 0.893 | 0.484 | 0.409 | 0.559 |
| 8 | 0.363 | 0.016 | 0.710 | 0.585 | 0.094 | 1.077 | 0.474 | 0.325 | 0.624 |
| 45 | NA | NA | NA | NA | NA | NA | NA | NA | NA |
| 7 | 0.435 | 0.015 | 0.855 | 0.534 | 0.054 | 1.013 | 0.470 | 0.353 | 0.558 |
| 28 | 0.384 | 0.119 | 0.650 | 0.593 | -0.009 | 1.195 | 0.486 | 0.236 | 0.736 |
| 36 | 0.329 | -0.218 | 0.875 | 0.672 | 0.095 | 1.250 | 0.499 | 0.377 | 0.621 |
| 25 | 0.394 | -0.134 | 0.922 | 0.567 | 0.079 | 1.055 | 0.472 | 0.388 | 0.555 |
| 43 | 0.369 | -0.282 | 1.020 | 0.635 | -0.044 | 1.314 | 0.482 | 0.358 | 0.606 |
| 41 | 0.418 | -0.245 | 1.080 | 0.529 | -0.136 | 1.193 | 0.448 | 0.337 | 0.560 |
| 15 | 0.351 | -0.140 | 0.843 | 0.634 | 0.077 | 1.191 | 0.482 | 0.356 | 0.608 |

FIGURE 7BII

```
                         SEQUENCE LISTING

<160> NUMBER OF SEQ ID NOS: 71

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
ccataattgc aaacgttctg                                               20

<210> SEQ ID NO 2
<211> LENGTH: 17
<212> TYPE: DNA
<213> ORGANISM: Artificial
<220> FEATURE:
<223> OTHER INFORMATION: Synthetic oligonucleotide

<400> SEQUENCE: 2
tttttttttt ttttttt                                                  17

<210> SEQ ID NO 3
<211> LENGTH: 20
<212> TYPE: DNA
<213> ORGANISM: Artificial
<220> FEATURE:
<223> OTHER INFORMATION: Synthetic oligonucleotide

<400> SEQUENCE: 3
ccataattgc aaagcttctg                                               20

<210> SEQ ID NO 4
<211> LENGTH: 14
<212> TYPE: DNA
<213> ORGANISM: Artificial
<220> FEATURE:
<223> OTHER INFORMATION: Synthetic oligonucleotide

<400> SEQUENCE: 4
tttttttttt tttt                                                     14

<210> SEQ ID NO 5
<211> LENGTH: 18
<212> TYPE: DNA
<213> ORGANISM: Artificial
<220> FEATURE:
<223> OTHER INFORMATION: Synthetic oligonucleotide

<400> SEQUENCE: 5
```

```
gttttttttt tttttttg                                              18

<210> SEQ ID NO 6
<211> LENGTH: 6
<212> TYPE: DNA
<213> ORGANISM: Artificial
<220> FEATURE:
<223> OTHER INFORMATION: Synthetic oligonucleotide

<400> SEQUENCE: 6 gacgtt                                                            6

<210> SEQ ID NO 7
<211> LENGTH: 17
<212> TYPE: DNA
<213> ORGANISM: Artificial
<220> FEATURE:
<223> OTHER INFORMATION: Synthetic oligonucleotide

<400> SEQUENCE: 7 ttttttttt tttttg                                                 17

<210> SEQ ID NO 8
<211> LENGTH: 20
<212> TYPE: DNA
<213> ORGANISM: Artificial
<220> FEATURE:
<223> OTHER INFORMATION: Synthetic oligonucleotide

<400> SEQUENCE: 8
tttttttttt tttttttttt                                            20

<210> SEQ ID NO 9
<211> LENGTH: 7
<212> TYPE: DNA
<213> ORGANISM: Artificial
<220> FEATURE:
<223> OTHER INFORMATION: Synthetic oligonucleotide

<400> SEQUENCE: 9 ttttttt                                                           7

<210> SEQ ID NO 10
<211> LENGTH: 20
<212> TYPE: DNA
<213> ORGANISM: Artificial
<220> FEATURE:
<223> OTHER INFORMATION: Synthetic oligonucleotide

<400> SEQUENCE: 10
ttgggggggg ggggggggtt                                            20

<210> SEQ ID NO 11
<211> LENGTH: 20
<212> TYPE: DNA
<213> ORGANISM: Artificial
<220> FEATURE:
<223> OTHER INFORMATION: Synthetic oligonucleotide

<400> SEQUENCE: 11
gggggggggg tttttttttt                                            20

<210> SEQ ID NO 12
<211> LENGTH: 18
<212> TYPE: DNA
<213> ORGANISM: Artificial
```

```
<220> FEATURE:
<223> OTHER INFORMATION: Synthetic oligonucleotide

<400> SEQUENCE: 12
gggggggggg ggggggtt                                                 18

<210> SEQ ID NO 13
<211> LENGTH: 6
<212> TYPE: DNA
<213> ORGANISM: Artificial
<220> FEATURE:
<223> OTHER INFORMATION: Synthetic oligonucleotide

<400> SEQUENCE: 13 gggggg                                                               6

<210> SEQ ID NO 14
<211> LENGTH: 18
<212> TYPE: DNA
<213> ORGANISM: Artificial
<220> FEATURE:
<223> OTHER INFORMATION: Synthetic oligonucleotide

<400> SEQUENCE: 14
ggtttttttt tttttttt                                                 18

<210> SEQ ID NO 15
<211> LENGTH: 20
<212> TYPE: DNA
<213> ORGANISM: Artificial
<220> FEATURE:
<223> OTHER INFORMATION: Synthetic oligonucleotide

<400> SEQUENCE: 15
cccccccccc cccccccccc                                               20

<210> SEQ ID NO 16
<211> LENGTH: 20
<212> TYPE: DNA
<213> ORGANISM: Artificial
<220> FEATURE:
<223> OTHER INFORMATION: Synthetic oligonucleotide

<400> SEQUENCE: 16
ggtttttttt ttttttttgg                                               20

<210> SEQ ID NO 17
<211> LENGTH: 7
<212> TYPE: DNA
<213> ORGANISM: Artificial
<220> FEATURE:
<223> OTHER INFORMATION: Synthetic oligonucleotide

<400> SEQUENCE: 17 ggggggg                                                              7

<210> SEQ ID NO 18
<211> LENGTH: 17
<212> TYPE: DNA
<213> ORGANISM: Artificial
<220> FEATURE:
<223> OTHER INFORMATION: Synthetic oligonucleotide

<400> SEQUENCE: 18
gggggggggg gggggt                                                   17
```

```
<210> SEQ ID NO 19
<211> LENGTH: 16
<212> TYPE: DNA
<213> ORGANISM: Artificial
<220> FEATURE:
<223> OTHER INFORMATION: Synthetic oligonucleotide

<400> SEQUENCE: 19
gggggggggg gagcct                                                    16

<210> SEQ ID NO 20
<211> LENGTH: 18
<212> TYPE: DNA
<213> ORGANISM: Artificial
<220> FEATURE:
<223> OTHER INFORMATION: Synthetic oligonucleotide

<400> SEQUENCE: 20
tggggggggg ggggggggt                                                 18

<210> SEQ ID NO 21
<211> LENGTH: 6
<212> TYPE: DNA
<213> ORGANISM: Artificial
<220> FEATURE:
<223> OTHER INFORMATION: Synthetic oligonucleotide

<400> SEQUENCE: 21 gagcct                                                                6

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide

<400> SEQUENCE: 22
aaaaaaaaaa aaaaaaaaaa                                                20

<210> SEQ ID NO 23
<211> LENGTH: 6
<212> TYPE: DNA
<213> ORGANISM: Artificial
<220> FEATURE:
<223> OTHER INFORMATION: Synthetic oligonucleotide

<400> SEQUENCE: 23 cccggg                                                                6

<210> SEQ ID NO 24
<211> LENGTH: 18
<212> TYPE: DNA
<213> ORGANISM: Artificial
<220> FEATURE:
<223> OTHER INFORMATION: Synthetic oligonucleotide

<400> SEQUENCE: 24
ttgggggggg gggggggg                                                  18

<210> SEQ ID NO 25
<211> LENGTH: 20
<212> TYPE: DNA
<213> ORGANISM: Artificial
<220> FEATURE:
<223> OTHER INFORMATION: Synthetic oligonucleotide
```

```
<400> SEQUENCE: 25
cgcgcgcgcg cgcgcgcgcg                                              20

<210> SEQ ID NO 26
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)
<220> FEATURE:
<221> NAME/KEY: Methylation
<222> LOCATION: (7)..(7)
<220> FEATURE:
<221> NAME/KEY: Methylation
<222> LOCATION: (9)..(9)
<220> FEATURE:
<221> NAME/KEY: Methylation
<222> LOCATION: (11)..(11)
<220> FEATURE:
<221> NAME/KEY: Methylation
<222> LOCATION: (13)..(13)
<220> FEATURE:
<221> NAME/KEY: Methylation
<222> LOCATION: (15)..(15)
<220> FEATURE:
<221> NAME/KEY: Methylation
<222> LOCATION: (17)..(17)
<220> FEATURE:
<221> NAME/KEY: Methylation
<222> LOCATION: (19)..(19)

<400> SEQUENCE: 26
cgcgcgcgcg cgcgcgcgcg                                              20

<210> SEQ ID NO 27
<211> LENGTH: 16
<212> TYPE: DNA
<213> ORGANISM: Artificial
<220> FEATURE:
<223> OTHER INFORMATION: Synthetic oligonucleotide

<400> SEQUENCE: 27
gggggggggg gacgct                                                  16

<210> SEQ ID NO 28
<211> LENGTH: 18
<212> TYPE: DNA
<213> ORGANISM: Artificial
<220> FEATURE:
<223> OTHER INFORMATION: Synthetic oligonucleotide

<400> SEQUENCE: 28
tttttttttt tttttttgg                                               18

<210> SEQ ID NO 29
<211> LENGTH: 12
<212> TYPE: DNA
<213> ORGANISM: Artificial
<220> FEATURE:
<223> OTHER INFORMATION: Synthetic oligonucleotide
```

```
<400> SEQUENCE: 29
cgcgcgcgcg cg                                                              12

<210> SEQ ID NO 30
<211> LENGTH: 12
<212> TYPE: DNA
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)
<220> FEATURE:
<221> NAME/KEY: Methylation
<222> LOCATION: (7)..(7)
<220> FEATURE:
<221> NAME/KEY: Methylation
<222> LOCATION: (9)..(9)
<220> FEATURE:
<221> NAME/KEY: Methylation
<222> LOCATION: (11)..(11)

<400> SEQUENCE: 30
cgcgcgcgcg cg                                                              12

<210> SEQ ID NO 31
<211> LENGTH: 20
<212> TYPE: DNA
<213> ORGANISM: Artificial
<220> FEATURE:
<223> OTHER INFORMATION: Synthetic oligonucleotide

<400> SEQUENCE: 31
gggggggggg aaaaaaaaaa                                                      20

<210> SEQ ID NO 32
<211> LENGTH: 16
<212> TYPE: DNA
<213> ORGANISM: Artificial
<220> FEATURE:
<223> OTHER INFORMATION: Synthetic oligonucleotide

<400> SEQUENCE: 32
gggggggggg cccgga                                                          16

<210> SEQ ID NO 33
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)
<220> FEATURE:
<221> NAME/KEY: Methylation
<222> LOCATION: (7)..(7)
<220> FEATURE:
<221> NAME/KEY: Methylation
```

```
<222> LOCATION: (9)..(9)
<220> FEATURE:
<221> NAME/KEY: Methylation
<222> LOCATION: (11)..(11)
<220> FEATURE:
<221> NAME/KEY: Methylation
<222> LOCATION: (13)..(13)
<220> FEATURE:
<221> NAME/KEY: Methylation
<222> LOCATION: (15)..(15)

<400> SEQUENCE: 33
cgcgcgcgcg cgcgcg                                                       16

<210> SEQ ID NO 34
<211> LENGTH: 9
<212> TYPE: DNA
<213> ORGANISM: Artificial
<220> FEATURE:
<223> OTHER INFORMATION: Synthetic oligonucleotide

<400> SEQUENCE: 34 ggggggggg                                                                9

<210> SEQ ID NO 35
<211> LENGTH: 6
<212> TYPE: DNA
<213> ORGANISM: Artificial
<220> FEATURE:
<223> OTHER INFORMATION: Synthetic oligonucleotide

<400> SEQUENCE: 35 tttttt                                                                   6

<210> SEQ ID NO 36
<211> LENGTH: 17
<212> TYPE: DNA
<213> ORGANISM: Artificial
<220> FEATURE:
<223> OTHER INFORMATION: Synthetic oligonucleotide

<400> SEQUENCE: 36
gggggggggg ggggggg                                                      17

<210> SEQ ID NO 37
<211> LENGTH: 5
<212> TYPE: DNA
<213> ORGANISM: Artificial
<220> FEATURE:
<223> OTHER INFORMATION: Synthetic oligonucleotide

<400> SEQUENCE: 37 ggggg                                                                    5

<210> SEQ ID NO 38
<211> LENGTH: 17
<212> TYPE: DNA
<213> ORGANISM: Artificial
<220> FEATURE:
<223> OTHER INFORMATION: Synthetic oligonucleotide

<400> SEQUENCE: 38
tggggggggg ggggggg                                                      17

<210> SEQ ID NO 39
<211> LENGTH: 8
<212> TYPE: DNA
```

```
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)
<220> FEATURE:
<221> NAME/KEY: Methylation
<222> LOCATION: (7)..(7)

<400> SEQUENCE: 39 cgcgcgcg                                                              8

<210> SEQ ID NO 40
<211> LENGTH: 11
<212> TYPE: DNA
<213> ORGANISM: Artificial
<220> FEATURE:
<223> OTHER INFORMATION: Synthetic oligonucleotide

<400> SEQUENCE: 40
tttttttttt t                                                         11

<210> SEQ ID NO 41
<211> LENGTH: 14
<212> TYPE: DNA
<213> ORGANISM: Artificial
<220> FEATURE:
<223> OTHER INFORMATION: Synthetic oligonucleotide

<400> SEQUENCE: 41
gggggggggg gggg                                                      14

<210> SEQ ID NO 42
<211> LENGTH: 17
<212> TYPE: DNA
<213> ORGANISM: Artificial
<220> FEATURE:
<223> OTHER INFORMATION: Synthetic oligonucleotide

<400> SEQUENCE: 42
gttttttttt ttttttt                                                   17

<210> SEQ ID NO 43
<211> LENGTH: 20
<212> TYPE: DNA
<213> ORGANISM: Artificial
<220> FEATURE:
<223> OTHER INFORMATION: Synthetic oligonucleotide

<400> SEQUENCE: 43
gggggggggg gggggggggg                                                20

<210> SEQ ID NO 44
<211> LENGTH: 20
<212> TYPE: DNA
<213> ORGANISM: Artificial
<220> FEATURE:
<223> OTHER INFORMATION: Synthetic oligonucleotide

<400> SEQUENCE: 44
gagagagaga gagagagaga                                                20
```

<210> SEQ ID NO 45
<211> LENGTH: 20
<212> TYPE: DNA
<213> ORGANISM: Artificial
<220> FEATURE:
<223> OTHER INFORMATION: Synthetic oligonucleotide

<400> SEQUENCE: 45
gtgtgtgtgt gtgtgtgtgt                                          20

<210> SEQ ID NO 46
<211> LENGTH: 4
<212> TYPE: DNA
<213> ORGANISM: Artificial
<220> FEATURE:
<223> OTHER INFORMATION: Synthetic oligonucleotide

<400> SEQUENCE: 46 gggg                                                            4

<210> SEQ ID NO 47
<211> LENGTH: 11
<212> TYPE: DNA
<213> ORGANISM: Artificial
<220> FEATURE:
<223> OTHER INFORMATION: Synthetic oligonucleotide

<400> SEQUENCE: 47
gggggggggg g                                                   11

<210> SEQ ID NO 48
<211> LENGTH: 4
<212> TYPE: DNA
<213> ORGANISM: Artificial
<220> FEATURE:
<223> OTHER INFORMATION: Synthetic oligonucleotide

<400> SEQUENCE: 48 tttt                                                            4

<210> SEQ ID NO 49
<211> LENGTH: 5
<212> TYPE: DNA
<213> ORGANISM: Artificial
<220> FEATURE:
<223> OTHER INFORMATION: Synthetic oligonucleotide

<400> SEQUENCE: 49 ttttt                                                           5

<210> SEQ ID NO 50
<211> LENGTH: 9
<212> TYPE: DNA
<213> ORGANISM: Artificial
<220> FEATURE:
<223> OTHER INFORMATION: Synthetic oligonucleotide

<400> SEQUENCE: 50 ttttttttt                                                       9

<210> SEQ ID NO 51
<211> LENGTH: 4
<212> TYPE: DNA
<213> ORGANISM: Artificial
<220> FEATURE:

<223> OTHER INFORMATION: Synthetic oligonucleotide

<400> SEQUENCE: 51 cgcg                                                                    4

<210> SEQ ID NO 52
<211> LENGTH: 6
<212> TYPE: DNA
<213> ORGANISM: Artificial
<220> FEATURE:
<223> OTHER INFORMATION: Synthetic oligonucleotide

<400> SEQUENCE: 52 cgcgcg                                                                  6

<210> SEQ ID NO 53
<211> LENGTH: 8
<212> TYPE: DNA
<213> ORGANISM: Artificial
<220> FEATURE:
<223> OTHER INFORMATION: Synthetic oligonucleotide

<400> SEQUENCE: 53 cgcgcgcg                                                                8

<210> SEQ ID NO 54
<211> LENGTH: 10
<212> TYPE: DNA
<213> ORGANISM: Artificial
<220> FEATURE:
<223> OTHER INFORMATION: Synthetic oligonucleotide

<400> SEQUENCE: 54
cgcgcgcgcg                                                             10

<210> SEQ ID NO 55
<211> LENGTH: 16
<212> TYPE: DNA
<213> ORGANISM: Artificial
<220> FEATURE:
<223> OTHER INFORMATION: Synthetic oligonucleotide

<400> SEQUENCE: 55
cgcgcgcgcg cgcgcg                                                      16

<210> SEQ ID NO 56
<211> LENGTH: 4
<212> TYPE: DNA
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)

<400> SEQUENCE: 56 cgcg                                                                    4

<210> SEQ ID NO 57
<211> LENGTH: 6
<212> TYPE: DNA
<213> ORGANISM: Artificial
<220> FEATURE:
<223> OTHER INFORMATION: Synthetic oligonucleotide

```
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)

<400> SEQUENCE: 57 cgcgcg                                                                        6

<210> SEQ ID NO 58
<211> LENGTH: 10
<212> TYPE: DNA
<213> ORGANISM: Artificial
<220> FEATURE:
<223> OTHER INFORMATION: Synthetic oligonucleotide
<220> FEATURE:
<221> NAME/KEY: Methylation
<222> LOCATION: (1)..(1)
<220> FEATURE:
<221> NAME/KEY: Methylation
<222> LOCATION: (3)..(3)
<220> FEATURE:
<221> NAME/KEY: Methylation
<222> LOCATION: (5)..(5)
<220> FEATURE:
<221> NAME/KEY: Methylation
<222> LOCATION: (7)..(7)
<220> FEATURE:
<221> NAME/KEY: Methylation
<222> LOCATION: (9)..(9)

<400> SEQUENCE: 58
cgcgcgcgcg                                                                   10

<210> SEQ ID NO 59
<211> LENGTH: 6
<212> TYPE: DNA
<213> ORGANISM: Artificial
<220> FEATURE:
<223> OTHER INFORMATION: Synthetic oligonucleotide

<400> SEQUENCE: 59 gacgct                                                                        6

<210> SEQ ID NO 60
<211> LENGTH: 16
<212> TYPE: DNA
<213> ORGANISM: Artificial
<220> FEATURE:
<223> OTHER INFORMATION: Synthetic oligonucleotide

<400> SEQUENCE: 60
gggggggggg gacgtt                                                            16

<210> SEQ ID NO 61
<211> LENGTH: 6
<212> TYPE: DNA
<213> ORGANISM: Artificial
<220> FEATURE:
<223> OTHER INFORMATION: Synthetic oligonucleotide

<400> SEQUENCE: 61 gagctt                                                                        6

<210> SEQ ID NO 62
```

```
<211> LENGTH: 16
<212> TYPE: DNA
<213> ORGANISM: Artificial
<220> FEATURE:
<223> OTHER INFORMATION: Synthetic oligonucleotide

<400> SEQUENCE: 62
gggggggggg gagctt                                                          16

<210> SEQ ID NO 63
<211> LENGTH: 6
<212> TYPE: DNA
<213> ORGANISM: Artificial
<220> FEATURE:
<223> OTHER INFORMATION: Synthetic oligonucleotide

<400> SEQUENCE: 63 cccgga                                                                      6

<210> SEQ ID NO 64
<211> LENGTH: 22
<212> TYPE: DNA
<213> ORGANISM: Artificial
<220> FEATURE:
<223> OTHER INFORMATION: Synthetic oligonucleotide

<400> SEQUENCE: 64
tccataacgt tgcaacgttc tg                                                   22

<210> SEQ ID NO 65
<211> LENGTH: 30
<212> TYPE: DNA
<213> ORGANISM: Artificial
<220> FEATURE:
<223> OTHER INFORMATION: Synthetic oligonucleotide

<400> SEQUENCE: 65
gggggggggg gggggggggg gggggggggg                                           30

<210> SEQ ID NO 66
<211> LENGTH: 24
<212> TYPE: DNA
<213> ORGANISM: Artificial
<220> FEATURE:
<223> OTHER INFORMATION: Synthetic oligonucleotide

<400> SEQUENCE: 66
ttagggttag ggttagggtt aggg                                                 24

<210> SEQ ID NO 67
<211> LENGTH: 20
<212> TYPE: DNA
<213> ORGANISM: Artificial
<220> FEATURE:
<223> OTHER INFORMATION: Synthetic oligonucleotide

<400> SEQUENCE: 67
ccataattcg aaacgttctg                                                      20

<210> SEQ ID NO 68
<211> LENGTH: 8
<212> TYPE: DNA
<213> ORGANISM: Artificial
<220> FEATURE:
<223> OTHER INFORMATION: Synthetic oligonucleotide

<400> SEQUENCE: 68
```

```
gagatctc                                                             8

<210> SEQ ID NO 69
<211> LENGTH: 13
<212> TYPE: DNA
<213> ORGANISM: Artificial
<220> FEATURE:
<223> OTHER INFORMATION: Synthetic oligonucleotide

<400> SEQUENCE: 69
ccataattgc aaa                                                      13

<210> SEQ ID NO 70
<211> LENGTH: 7
<212> TYPE: DNA
<213> ORGANISM: Artificial
<220> FEATURE:
<223> OTHER INFORMATION: Synthetic oligonucleotide

<400> SEQUENCE: 70 cgttctg                                                              7

<210> SEQ ID NO 71
<211> LENGTH: 7
<212> TYPE: DNA
<213> ORGANISM: Artificial
<220> FEATURE:
<223> OTHER INFORMATION: Synthetic oligonucleotide

<400> SEQUENCE: 71 gcttctg                                                              7
```

DIAGNOSIS OF SYSTEMIC LUPUS ERYTHEMATOSUS USING OLIGONUCLEOTIDES ANTIGENS

FIELD OF THE INVENTION

The present invention relates to oligonucleotide antigens useful in diagnosing an autoimmune disorder such as systemic lupus erythematosus (SLE) in a subject.

BACKGROUND OF THE INVENTION

Systemic lupus erythematosus (SLE), a prototypic autoimmune disease, is associated with a large spectrum of autoantibodies. IgG antibodies to more than 100 different antigens including DNA, nucleosomes, histones, viral antigens, transcription factors and more have been reported in different SLE patients (Sherer et al., 2004, Semin. Arthritis. Rheum. 34:501-37). Surprisingly, there is no serologic diagnosis of SLE and SLE is diagnosed on the basis of eleven criteria defined by the American College of Rheumatology (ACR). These criteria include malar rash, discoid rash, photosensitivity, oral ulcers, arthritis, serositis, renal disorder, neurologic disorder, hematologic disorder (e.g., leucopenia, lymphopenia, hemolytic anemia or thrombocytopenia), immunologic disorder and antibody abnormalities (particularly anti-nuclear antibodies (ANA) and anti-DNA antibodies) (Tan et al., 1997, Arthritis Rheum 1997, 40:1725). According to these criteria, subjects can be clinically diagnosed with SLE if they meet at least four of the eleven criteria. Recently, the Systemic Lupus Collaborating Clinics (SLICC) revised these criteria, as reviewed in Petri et al. (Arthritis and Rheumatism, 2012, Vol. 64, pages 2677-2686). Nevertheless, SLE is still possible even in case when less than four criteria are present.

Although the precise pathology of SLE is not clear, it is widely accepted that autoantibodies play an important role. Autoantibodies to DNA are highly heterogeneous with respect to their avidity, immunoglobulin subclass composition, cross-reactivity and complement fixing ability. A number of techniques have been utilized for DNA autoantibodies detection, including immunofluorescent assays (IFA), enzyme-linked immunosorbent assays (ELISAs) and radioimmunoassays (RIA). However, the clinical value of anti-double stranded DNA (dsDNA) antibodies largely depends on the assay principle and analytical variables of the methods used to quantitate and immunologically characterize them.

Park and coworkers (Park et al., "Primary Structures and Chain Dominance of Anti-DNA Antibodies", Mol. Cells, 2001, Vol. 11(1), pages 55-63) studied the relative involvement of heavy and light chains of several anti-DNA autoantibodies in their interaction with several dsDNA targets, amongst which is $(GA)_2$-$(TC)_2$ (corresponding to SEQ ID NO: 68 as described herein).

Herkel and coworkers (Herkel et al., "Monoclonal antibody to a DNA-binding domain of p53 mimics charge structure of DNA: anti-idiotypes to the anti-p53 antibody are anti-DNA", Eur. J. Immunol., 2004, Vol. 34, pages 3623-3632), to some the present inventors, studied two anti-idiotypic monoclonal antibodies (Idi1 and Idi2) raised against PAb-421 (a prototypic monoclonal antibody that reacts with the C-terminal DNA-binding domain of p53). These antibodies were found to specifically recognize both PAb-421 and DNA. In addition, both antibodies were able to specifically bind single-stranded poly-G targets, G20 (corresponding to SEQ ID NO: 43) and T2G16T2 (corresponding to SEQ ID NO: 10 as described herein). However, these antibodies did not bind poly-T, poly-C or poly-A targets.

P. Lenert ("Nucleic acid sensing receptors in systemic lupus erythematosus: development of novel DNA- and/or RNA-like analogues for treating lupus", Clinical and Experimental Immunology, 2010, Vol. 161, pages 208-222) reviewed genetic, epigenetic, gender-related and environmental factors which are believed to contribute to the pathogenesis of autoimmunity in systemic lupus erythematosus (SLE). Lenert further reviewed several inhibitory oligonucleotides (INH-ODN) aimed to prevent the development of autoimmunity, amongst which is $(TTAGGG)_4$ (corresponding to present SEQ ID NO: 66).

International Patent Application Publication No. WO 11/099012, to some the present inventors, relates to methods and kits for diagnosing systemic lupus erythematosus (SLE) in a subject, using a specific antibody profile. The '012 publication discloses patients having, inter alia, increased IgG reactivity to Epstein-Barr Virus (EBV). Additional patents and patent applications disclosing diagnosis of autoimmune diseases using a specific antibody profile include WO 10/055510, WO 12/052994, US 2005/0260770 and U.S. Pat. No. 8,010,298. Further, US Patent Application Publication No. 2012/0122720 relates to recognizing the development of cardiovascular disease, e.g., acute myocardial infarction process in an individual. International Patent Application Publication No. WO 2014/091490, of some the present inventors, relates to methods for diagnosing SLE or scleroderma by using specific antibody profiles against an array of antigens derived from the Epstein-Ban Virus (EBV).

One of the most difficult challenges in clinical management of complex autoimmune diseases such as SLE is the accurate and early identification of the disease in a patient. There remains a need for improved diagnostic methods and kits useful in diagnosing SLE in a subject.

SUMMARY OF THE INVENTION

The present invention provides methods and kits for diagnosing an autoimmune disorder, particularly systemic lupus erythematosus (SLE). The present invention further provides antigen probe arrays for practicing such a diagnosis, and antigen probe sets for generating such arrays.

The present invention is based, in part, on the unexpected results obtained when testing the antibody reactivity of SLE patients compared to other autoimmune conditions, particularly scleroderma and pemphigus patients, as well as in comparison to healthy controls. Surprisingly, increased immunoglobulin G (IgG) and IgM reactivities to specific polynucleotide antigens were found in the tested SLE patients, compared to healthy controls. Thus, the present invention provides unique oligonucleotide antigens, indicative to SLE. The present invention further provides antigen-autoantibody reactivity patterns relevant to SLE. In particular embodiments, the present invention provides highly specific, reliable, accurate and discriminatory assays for diagnosing SLE, based on the indicative oligonucleotide antigens, or on reactivity patterns thereof.

Thus, according to embodiments of the invention, there are provided novel methods for diagnosing and monitoring the progression of SLE. According to embodiments of the invention, the methods comprise determining the reactivity of antibodies in a sample obtained or derived from a subject to at least one oligonucleotide antigen as described herein. The methods of the invention further comprise a step of comparing the reactivity of antibodies in the sample to the at least one oligonucleotide antigen to a control reactivity to said at least one oligonucleotide antigen. According to certain embodiments, a significantly higher reactivity of the antibodies in the sample compared to the reactivity of the healthy control is an indication that the subject is afflicted with SLE.

Thus, according to a first aspect, the present invention provides a method of diagnosing systemic lupus erythematosus (SLE) in a subject, the method comprising the steps of obtaining a sample from the subject, determining the reactivity of antibodies in the sample to at least one oligonucleotide antigen selected from the groups consisting of: GTTTTTTTTTTTTTTT (SEQ ID NO: 42), TTTTTTTTTTTTTTTG (SEQ ID NO: 7), GTTTTTTTTTTTTTTTG (SEQ ID NO: 5), TTTTTTTTTTTTTTTGG (SEQ ID NO: 28), and TTTTTTTTTTTTTTTTTT (SEQ ID NO: 8); or CCATAATTGCAAACGTTCTG (SEQ ID NO: 1) and CCATAATTGCAAAGCTTCTG (SEQ ID NO: 3); or AAAAAAAAAAAAAAAAAAAA (SEQ ID NO: 22); and comparing the reactivity of antibodies in the sample to a reactivity of a healthy control; wherein a significantly higher reactivity of the antibodies in the sample compared to the reactivity of the healthy control is an indication that the subject is afflicted with SLE.

As clearly evident, GTTTTTTTTTTTTTTT (SEQ ID NO: 42), TTTTTTTTTTTTTTTG (SEQ ID NO: 7), GTTTTTTTTTTTTTTTG (SEQ ID NO: 5), TTTTTTTTTTTTTTTGG (SEQ ID NO: 28), and TTTTTTTTTTTTTTTTTT (SEQ ID NO: 8) share a common sequential consensus motif, namely a stretch of at least 16 consecutive thymine nucleotides, preceded or followed by one or two guanosine residues. As further evident, CCATAATTGCAAACGTTCTG (SEQ ID NO: 1) and CCATAATTGCAAAGCTTCTG (SEQ ID NO: 3) also share a common sequential consensus motif, namely CCATAATTGCAAA (SEQ ID NO: 69), followed by either CGTTCTG (SEQ ID NO: 70) or GCTTCTG (SEQ ID NO: 71).

According to another aspect, the present invention provides a method of diagnosing systemic lupus erythematosus (SLE) in a subject, the method comprising the steps of obtaining a sample from the subject; determining the reactivity of antibodies in the sample to a plurality of oligonucleotide antigens selected from the group consisting of SEQ ID NOs: 1, 3, 5, 7, 8, 10, 17, 18, 22, 28, 34, 36, 38, 41, 42, 43, 44, 65, 66 and 67; and comparing the reactivity of antibodies in the sample to a reactivity of a healthy control; wherein a significantly higher reactivity of the antibodies in the sample compared to the reactivity of the healthy control is an indication that the subject is afflicted with SLE.

In certain embodiments, a significantly higher reactivity of the antibodies in the sample compared to the reactivity of the healthy control is an indication that the subject is of increased likelihood to be afflicted with SLE. In other certain embodiments, where the reactivity of the antibodies in the sample compared to the reactivity of the healthy control is not significantly higher, where the reactivity of the antibodies in the sample compared to the reactivity of the healthy control is the same, where the reactivity of the antibodies in the sample compared to the reactivity of the healthy control is lower or where the reactivity of the antibodies in the sample compared to the reactivity of the healthy control is significantly lower, it is an indication that the subject is of decreased likelihood to be afflicted with SLE. Each possibility represents a separate embodiment of the present invention.

In certain embodiments of the methods of the present invention, the methods are preceded by a step comprising obtaining or deriving a sample from the subject. In certain embodiments, the sample is obtained or derived from the subject by non-invasive means or methods.

In certain embodiments, determining the reactivity of antibodies in the sample to a plurality of oligonucleotide antigens produces a reactivity pattern, used for the diagnosis of SLE in the subject. Thus, according to exemplary embodiments of the invention, the reactivity pattern of antibodies in the sample to the plurality of oligonucleotide antigens is compared to the reactivity pattern of antibodies in a sample corresponding to healthy control subjects to said plurality of oligonucleotide antigens, wherein a significant difference (typically elevation) between the reactivity pattern of the sample and the reactivity pattern of healthy controls indicates that the subject is afflicted with, or in other embodiments has increased likelihood for having SLE. Conveniently, the reactivity patterns are calculated and compared using e.g. learning and pattern recognition algorithms as described herein.

According to some embodiments, the at least one oligonucleotide antigen is selected from the group consisting of SEQ ID NOs: 42, 7, 5, 28 and 8. According to additional embodiments, the at least one oligonucleotide antigen is selected from SEQ ID NOs: 1 or 3. According to additional embodiments, the at least one oligonucleotide antigen is SEQ ID NO: 22. Each possibility represents a separate embodiment of the invention.

According to another embodiment, the reactivity of antibodies comprises IgG and IgM reactivities. According to another embodiment, the significantly higher reactivity of the antibodies in the sample comprises increased IgG and/or IgM reactivities. According to another embodiment, the increased IgM reactivity is of at least one oligonucleotide antigen selected from the group consisting of SEQ ID NOs: 42, 7, 5, 28, 8, 1, 3 and 22. According to another embodiment, the increased IgG reactivity is of at least one oligonucleotide antigen selected from the group consisting of SEQ ID NO: SEQ ID NOs: 42, 7, 5, 28, 8, 1, 3 and 22. Each possibility represents a separate embodiment of the invention.

In certain embodiments, the subject is positive for antibodies to double stranded DNA (dsDNA). In other certain embodiments, the subject is negative for antibodies to dsDNA. Unless otherwise indicated, all single stranded DNA (ssDNA) and dsDNA samples are calf ssDNA and dsDNA samples.

According to additional embodiments of the methods of the present invention, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. In certain embodiments, the sample is obtained or derived from the subject by non-invasive means or methods.

According to certain embodiments of the methods of the present invention, the control is selected from the group consisting of a sample from at least one healthy individual, a panel of control samples from a set of healthy individuals, and a stored set of data from healthy individuals. Each possibility represents a separate embodiment of the invention. Typically, a healthy individual is a subject not afflicted with SLE (or any other form of lupus). In another embodiment, a healthy individual is a subject not afflicted with an autoimmune disease (e.g., scleroderma).

According to another embodiment, the method comprises determining the reactivity of antibodies in the sample to a plurality of oligonucleotide antigens.

According to another embodiment, the method comprises determining the reactivity of antibodies in the sample to at least one oligonucleotide antigen selected from the group consisting of SEQ ID NO: 42, SEQ ID NO: 7, SEQ ID NO: 5, SEQ ID NO: 28, SEQ ID NO: 8, SEQ ID NO: 1, SEQ ID NO: 3, and SEQ ID NO: 22; and to at least one additional oligonucleotide antigen selected from the group consisting of SEQ ID NOs: 1, 3, 5, 7, 8, 10, 17, 18, 22, 28, 34, 36, 38, 41, 42, 43, 44, 65, 66 and 67. Each possibility represents a separate embodiment of the invention.

According to another embodiment, the method comprises determining the reactivity of antibodies in the sample to at least two oligonucleotide antigens selected from the group consisting of SEQ ID NO: 42, SEQ ID NO: 7, SEQ ID NO: 5, SEQ ID NO: 28, SEQ ID NO: 8, SEQ ID NO: 1, SEQ ID NO: 3, and SEQ ID NO: 22. Each possibility represents a separate embodiment of the invention.

According to another embodiment, the plurality of antigens is used in the form of an antigen probe set, an antigen array, or an antigen chip.

According to another aspect, the present invention provides an antigen probe set comprising a plurality of oligonucleotide antigen probes selected from the group consisting of SEQ ID NOs: 1, 3, 5, 7, 8, 10, 17, 18, 22, 28, 34, 36, 38, 41, 42, 43, 44, 65, 66 and 67. In another embodiment, the antigen probe set comprises the oligonucleotide antigen probes of SEQ ID NOs: 1, 3, 5, 7, 8, 10, 17, 18, 22, 28, 34, 36, 38, 41, 42, 43, 44, 65, 66 and 67.

According to another aspect, the present invention provides an article of manufacture comprising the antigen probe set described above.

In certain embodiments, the article of manufacture is in the form of an antigen probe array or in the form of an antigen chip or in the form of a dipstick or in the form of a lateral flow test or in the form of an ELISA plate or in the form of a Quanterix system or in the form of a dipsticks or any other platform known to those skilled in the art. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use of the kit for diagnosing SLE.

According to another aspect, there is provided use of the at least one oligonucleotide antigen selected from the group consisting of: SEQ ID NOs: 1, 3, 5, 7, 8, 10, 17, 18, 22, 28, 34, 36, 38, 41, 42, 43, 44, 65, 66 and 67, for the preparation of a diagnostic kit for diagnosing SLE in a subject. Each possibility represents a separate embodiment of the invention. The diagnostic kit is, in some embodiments, useful for determining the reactivity of antibodies in a sample, thereby determining the reactivity pattern of the sample to the at least one oligonucleotide antigen. In some embodiments, a significant difference (e.g., increase) between the reactivity pattern of the sample compared to a reactivity pattern of a control sample is an indication for SLE.

Other objects, features and advantages of the present invention will become clear from the following description and drawings.

BRIEF DESCRIPTION OF THE DRAWINGS

FIG. 6A-6B show IgG and IgM binding to (CG)10 (SEQ ID NO: 25) in healthy subjects, and SSc and SLE patients. FIG. 6A—IgM; FIG. 6B—IgG.

FIGS. 7AI,7AII, 7BI and 7BII provide a table of oligonucleotides with increased IgG (7AI-7AII) and IgM (7BI-7BII) binding in SLE patients compared to healthy controls.

DETAILED DESCRIPTION OF THE INVENTION

Figure 1:
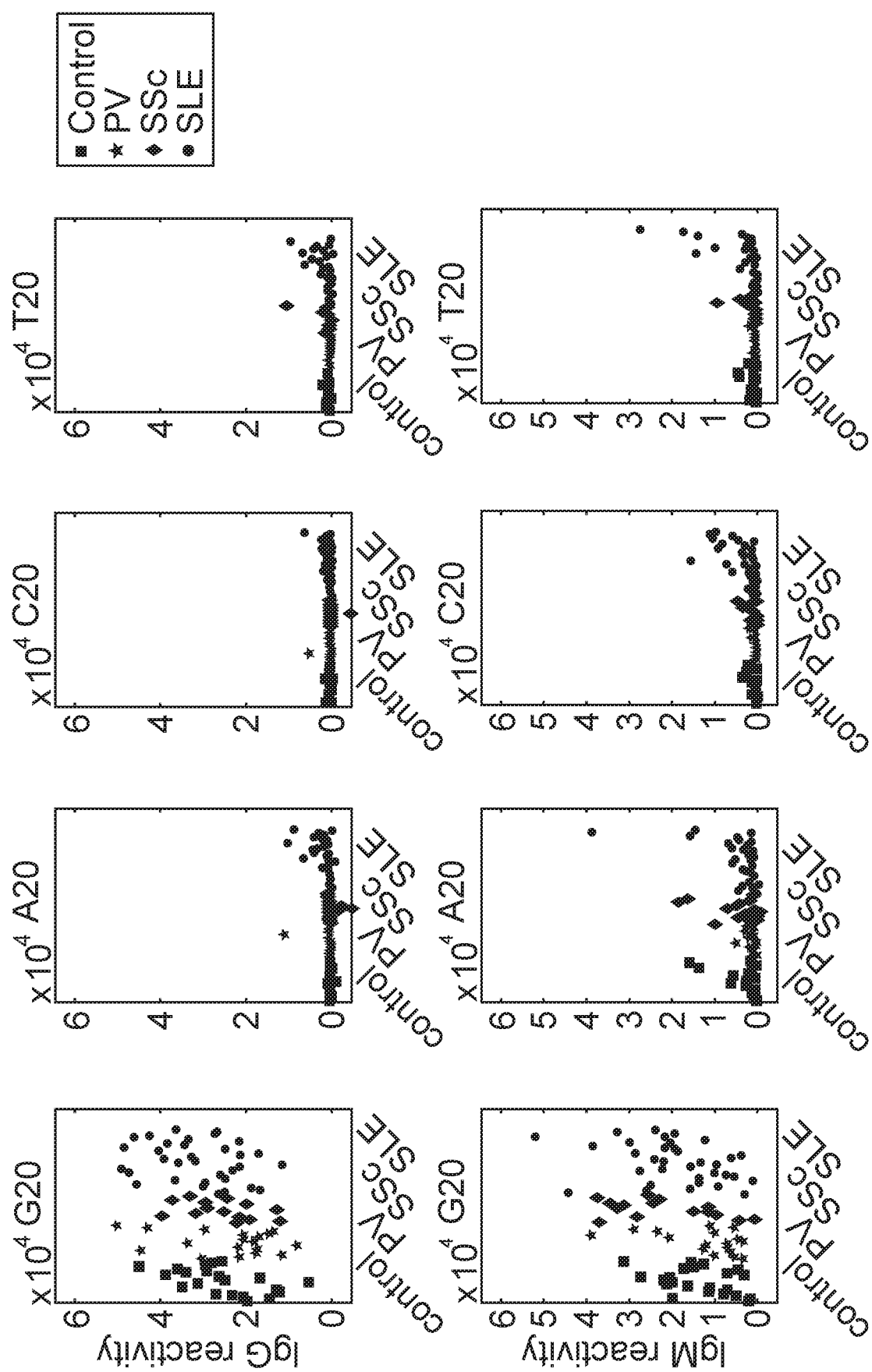
FIG. 1 depicts individual IgM and IgG reactivities to A20 (SEQ ID NO: 22), C20 (SEQ ID NO: 15), G20 (SEQ ID NO: 43) and T20 (SEQ ID NO: 8) in sera from healthy subjects (boxes), pemphigus vulgaris (PV) patients (stars), scleroderma (SSc) patients (diamonds), and SLE patients (circles). Subjects were ordered from left to right according to their reactivity to dsDNA.

The present invention provides methods of diagnosing an autoimmune disease or disorder, specifically systemic lupus erythematosus (SLE), in a subject. The present invention further provides antigen probe sets or arrays for practicing such a diagnosis, and identifies specific antigen probe sets for generating such sets or arrays.

Without wishing to be bound by any particular theory or mechanism of action, the invention is based, in part, on the finding of unique oligonucleotide antigens highly distinctive between healthy subjects and SLE patients. The invention is further based on the finding that the antibody reactivity profile in serum of SLE patients was clearly distinct from healthy control individuals. Although serum autoantibodies have been extensively investigated in SLE, the unique antibody immune signatures as described herein have not been described before. Advantageously, the unique antibody signatures of the present disclosure provide highly sensitive and specific assays for diagnosing SLE, particularly of SLE subjects positive to dsDNA.

The present invention provides, in some embodiments, unique antigen-autoantibody reactivity patterns particularly relevant to SLE. In the course of investigating anti-DNA autoantibodies, the inventors examined the reactivity of IgM and IgG antibodies in the sera of healthy persons and those diagnosed with systemic lupus erythematosus (SLE), scleroderma (SSc), or pemphigus vulgaris (PV) to a variety of oligonucleotide antigens, using antigen microarray and informatics analysis. Surprisingly, all of the human subjects studied, irrespective of health or autoimmune disease, manifested relatively high amounts of IgG antibodies binding to G20 (SEQ ID NO: 43), but not to A20 (SEQ ID NO: 22), C20 (SEQ ID NO: 15), and T20 (SEQ ID NO: 8). Nevertheless, SLE patients showed increased IgG and IgM reactivities to specific oligonucleotide antigens other than to G20 (SEQ ID NO: 43), which are highly indicative of SLE, such as GTTTTTTTTTTTTTTTT (SEQ ID NO: 42), TTTTTTTTTTTTTTTTG (SEQ ID NO: 7), GTTTTTTTTTTTTTTTG (SEQ ID NO: 5), TTTTTTTTTTTTTTTGG (SEQ ID NO: 28), TTTTTTTTTTTTTTTTTTT (SEQ ID NO: 8), CCATAATTGCAAACGTTCTG (SEQ ID NO: 1), CCATAATTGCAAAGCTTCTG (SEQ ID NO: 3), and AAAAAAAAAAAAAAAAAAAA (SEQ ID NO: 22).

As exemplified herein below, in certain assays, several tested oligonucleotide antigens partly overlapped with the reactivities of calf double strand DNA (dsDNA) and single strand DNA (ssDNA). However, a subset of oligonucleotides showed similar or advantageously higher sensitivity and/or specificity compared to dsDNA and ssDNA. The advantages of using short, single-stranded, synthetic oligonucleotide sequences over oligonucleotides derived from biological sources are manifold, amongst which fidelity in sequence and ease and cost of production. As noted in the background section herein, the clinical value of anti-dsDNA antibodies largely depends on the assay principle and analytical variables of the methods used to quantitate and immunologically characterize them. Embodiments of the invention provide for improved assays and methods having advantageous properties for clinical diagnosis compared to hitherto known methods.

The present invention further discloses that SLE patients may be serologically differentiated from scleroderma patients. It is disclosed herein for the first time that SLE subjects have a unique serological signature which can be used to discriminate the subjects from subjects afflicted with scleroderma. The unique serological signature of SLE subjects includes increased IgG reactivities as well as decreased IgM reactivities to certain oligonucleotide antigens. Thus, in some embodiments, the present invention provides assays for discriminating and differentiating between subjects afflicted with SLE and subjects afflicted with scleroderma.

According to another aspect, the present invention provides a method of differentiating between subjects afflicted with SLE and subjects afflicted with scleroderma, the method comprising obtaining a sample from the subject; determining the reactivity of antibodies in the sample to at least one oligonucleotide antigen selected from the group consisting of SEQ ID NO: 1, 3, 5, 9-15, 17-20, 22-23, 25-34 and 37-39, thereby determining the reactivity pattern of the sample; and comparing the reactivity pattern of the sample to a control reactivity pattern; wherein a significantly different reactivity pattern of the antibodies in the sample compared to the control reactivity sample is an indication that the subject is afflicted with SLE.

In one embodiment, the reactivity pattern of the sample comprises increased IgG reactivity. In particular embodiments, the increased IgG reactivity is of at least one oligonucleotide antigen selected from the group consisting of SEQ ID NO: 1, 3, 5, 9-15, 17-20, 22-23, 25-34 and 37-39. In another embodiment, the reactivity pattern of the sample comprises decreased IgM reactivity. In particular embodiments, the decreased IgM reactivity is of at least one oligonucleotide antigen selected from SEQ ID NO: 25 and 26.

According to some embodiments of the methods for SLE diagnosis in a subject in need thereof, the methods comprises determining the reactivity of antibodies in a sample obtained from the subject to at least one oligonucleotide antigen selected from the group consisting of SEQ ID NOs: 42, 7, 5, 28, 8, 1, 3 and 22, or a subset or combination thereof, thereby determining the reactivity pattern of the sample, and determining the subject as a subject afflicted with SLE if the reactivity pattern of the antibodies in the sample is significantly different compared to control.

According to a first aspect, the present invention provides a method of diagnosing systemic lupus erythematosus (SLE) in a subject, the method comprising the steps of obtaining a sample from the subject, determining the reactivity of antibodies in the sample to at least one oligonucleotide antigen selected from the groups consisting of: SEQ ID NO: 42, SEQ ID NO: 7, SEQ ID NO: 5, SEQ ID NO: 28, and SEQ ID NO: 8; or SEQ ID NO: 1 and SEQ ID NO: 3; or SEQ ID NO: 22; and comparing the reactivity of antibodies in the sample to a reactivity of a healthy control; wherein a significantly higher reactivity of the antibodies in the sample compared to the reactivity of the healthy control is an indication that the subject is afflicted with SLE.

According to a related aspect, the present invention provides a method of diagnosing systemic lupus erythematosus (SLE) in a subject, the method comprising the steps of determining the reactivity of antibodies in a sample obtained from a subject to at least one oligonucleotide antigen selected from the group consisting of: SEQ ID NO: 42, SEQ ID NO: 7, SEQ ID NO: 5, SEQ ID NO: 28, and SEQ ID NO: 8; or SEQ ID NO: 1 and SEQ ID NO: 3; or SEQ ID NO: 22; and comparing the reactivity of antibodies in the sample to a reactivity of a healthy control; wherein a significantly higher reactivity of the antibodies in the sample compared to the reactivity of the healthy control is an indication that the subject is afflicted with SLE.

According to another aspect, the present invention provides a method of diagnosing systemic lupus erythematosus (SLE) in a subject, the method comprising the steps of obtaining a sample from the subject; determining the reactivity of antibodies in the sample to a plurality of oligonucleotide antigens selected from the group consisting of SEQ ID NOs: 1, 3, 5, 7, 8, 10, 17, 18, 22, 28, 34, 36, 38, 41, 42, 43, 44, 65, 66 and 67; and comparing the reactivity of antibodies in the sample to a reactivity of a healthy control; wherein a significantly higher reactivity of the antibodies in the sample compared to the reactivity of the healthy control is an indication that the subject is afflicted with SLE.

According to a related aspect, the present invention provides a method of diagnosing systemic lupus erythematosus (SLE) in a subject, the method comprising the steps of: determining the reactivity of antibodies in a sample obtained from the subject to a plurality of oligonucleotide antigens selected from the group consisting of SEQ ID NOs: 1, 3, 5, 7, 8, 10, 17, 18, 22, 28, 34, 36, 38, 41, 42, 43, 44, 65, 66 and 67; and comparing the reactivity of antibodies in the sample to a reactivity of a healthy control; wherein a significantly higher reactivity of the antibodies in the sample compared to the reactivity of the healthy control is an indication that the subject is afflicted with SLE.

The nomenclature used to refer to the oligonucleotide sequence of each oligonucleotide antigen disclosed in the present invention is as follows: an oligonucleotide antigen consisting of the oligonucleotide sequence of $X_2Y_3Z_2$, i.e. two oligonucleotides of X followed by three oligonucleotides of Y followed by two oligonucleotides of Z is labeled as X2Y3Z2, (X)2(Y)3(Z)2, or XXYYYZZ, or referred to by its corresponding SEQ ID NO. It should be understood that in this example, X, Y and Z may relate to more than one oligonucleotide, e.g. to 2-20 oligonucleotides. Therefore, an oligonucleotide antigen consisting of the oligonucleotide sequence of $X_2$, wherein X is a stretch of e.g. two oligonucleotides, e.g. YZ, is labeled as X2, (X)2, or YZYZ, or referred to by its corresponding SEQ ID NO.

The terms "systemic lupus erythematosus", "lupus" and "SLE" as used herein are interchangeable, and generally refer to an autoimmune disease characterized by the criteria set by the 1982 American College of Rheumatology (ACR) for the diagnosis of SLE, and/or by the Systemic Lupus Collaborating Clinics (SLICC) revised criteria, reviewed in Petri et al. (Arthritis and Rheumatism, 2012, Vol. 64, pages 2677-2686).

The terms "oligonucleotide antigen" and "antigen" as used herein are interchangeable, and generally refer to a stretch of contiguous nucleotides of a certain length. Unless otherwise indicated, the term "oligonucleotide antigen" as used herein relates to a nucleotide sequence of between 15 and 40 nucleotides in length, alternatively between 17 and 28 nucleotides in length, or between 18-25 nucleotides in length. In certain embodiments, an oligonucleotide antigen consists of at least 4, at least 5, at least 6, at least 7, at least 8, at least 9, at least 10, at least 16, or more contiguous nucleotides. Each possibility represents a separate embodiment of the invention. In certain embodiments, an antigen consists of not more than 50, not more than 45, not more than 40, not more than 35, not more than 30, not more than 25, not more than 20, not more than 16, or less contiguous nucleotides. Each possibility represents a separate embodiment of the invention. In certain embodiments, an antigen consists of 10-30, 15-25 or 17-20 contiguous nucleotides. In certain embodiments, an antigen consists of 17, 18, 19 or 20 contiguous nucleotides.

The term "healthy control" as used herein refers to a healthy individual, a plurality of healthy individuals, a data set or value corresponding to or obtained from a healthy individual or a plurality of healthy individuals.

The term "sample" as used herein refers to any composition comprising a biological material obtained or derived from a subject. Non-limiting examples of samples according to the present invention are any kind of a biological tissue or a fluid which comprises antibodies.

As used herein, the "reactivity of antibodies in a sample" or "reactivity of an antibody in a sample" to "an antigen" or to "a plurality of antigens" refers to the immune reactivity of at least one antibody in the sample to at least one specific antigen selected from the plurality of antigens. The immune reactivity of the antibody to the antigen, i.e. its ability to specifically bind the antigen, may be used to determine the amount of the antibody in the sample. The calculated levels of each one of the tested antibodies in the sample are collectively referred to as the reactivity pattern of the sample to these antigens. The reactivity pattern of the sample reflects the levels of each one of the tested antibodies in the sample, thereby providing a quantitative assay. In a preferred embodiment, the antibodies are quantitatively determined A "significant difference" between reactivity patterns refers, in different embodiments, to a statistically significant difference, or in other embodiments to a significant difference as recognized by a skilled artisan. In yet another preferred embodiment, a significant (quantitative) difference between the reactivity pattern of the sample obtained from the subject compared to the control reactivity pattern is an indication that the subject is afflicted with SLE. In specific embodiments, up-regulation or higher reactivity of the reactivity of an antibody in a sample to an antigen refers to an increase (i.e., elevation) of about at least two, about at least three, about at least four, or about at least five times higher (i.e., greater) than the reactivity levels of the antibody to the antigen in the control. In another embodiment, down-regulation or lower reactivity of the reactivity of an antibody in a sample to an antigen refers to a decrease (i.e., reduction) of about at least two, about at least three, about at least four, or about at least five times lower than the reactivity levels of the antibody to the antigen in the control.

In certain embodiments, a subset of oligonucleotide antigen consists of the sequence CCATAATTGCAAACGTTCTG (SEQ ID NO: 1), T17 (SEQ ID NO: 2), CCATAATTGCAAAGCTTCTG (SEQ ID NO: 3), G1T16G1 (SEQ ID NO: 5), G1OT10 (SEQ ID NO: 11) and G16T2 (SEQ ID NO: 12), wherein each possibility or combination thereof represents a separate embodiment of the invention. As exemplified herein below, the subset showed similar or advantageously higher sensitivity compared to dsDNA. In another embodiment, a subset of oligonucleotide antigen comprises T20 (SEQ ID NO: 8), C20 (SEQ ID NO: 15) and A20 (SEQ ID NO: 22), wherein each possibility or combination thereof represents a separate embodiment of the invention.

According to some embodiments, the at least one oligonucleotide antigen is an oligonucleotide sequence comprising at least 5, 6, 7, 8, 9, 10, 11, 12, 13, 14, 15, 16, 17, 18, 19 or 20 contiguous adenine nucleotides. According to another embodiment, the oligonucleotide sequence comprises at most 20 contiguous adenine nucleotides. According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous thymine nucleotides. According to another embodiment, the oligonucleotide sequence comprises at most 20 contiguous thymine nucleotides.

According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous cytosine nucleotides. According to another embodiment, the oligonucleotide sequence comprises at most 20 contiguous cytosine nucleotides. According to additional embodiments, the at least one oligonucleotide antigen is an oligonucleotide sequence comprising 5-17, 6-17, 7-17, 8-17, 9-17, 10-17, 11-17, 12-17, 13-17, 14-17, 15-17, 16-17, or at most 17 contiguous guanine nucleotides.

According to some embodiments, the at least one oligonucleotide antigen is selected from the group consisting of SEQ ID NOs: 42, 7, 5, 28 and 8. According to additional embodiments, the at least one oligonucleotide antigen is selected from SEQ ID NOs: 1 or 3. According to additional embodiments, the at least one oligonucleotide antigen is SEQ ID NO: 22. Each possibility represents a separate embodiment of the invention.

It should be understood each oligonucleotide antigen according to the present invention may be bound by IgM antibodies and/or IgG antibodies found or isolated from a sample obtained or derived from the tested subject. Since the relative amounts of IgM antibodies and IgG antibodies against a certain epitope or antigen naturally change over the course of time, each oligonucleotide antigen according to the present invention may be bound by IgM antibodies, IgG antibodies or both. In certain embodiments, the reactivity of antibodies means the reactivity of IgG antibodies. In certain embodiments, the reactivity of antibodies means the reactivity of IgM antibodies. According to another embodiment, the significantly higher reactivity of the antibodies in the sample means increased IgG reactivity. According to another embodiment, the significantly higher reactivity of the antibodies in the sample comprises increased IgM reactivity.

According to another embodiment, the increased IgM reactivity is of at least one oligonucleotide antigen selected from the group consisting of SEQ ID NO: 1 (CCATAATTGCAAACGTTCTG), SEQ ID NO: 2 (T17), SEQ ID NO: 3 (CCATAATTGCAAAGCTTCTG), SEQ ID NO: 4 (T14), SEQ ID NO: 5 (G1T16G1), SEQ ID NO: 6 (GACGTT), SEQ ID NO: 7 (T16G1), SEQ ID NO: 8 (T20), SEQ ID NO: 9 (T7), and SEQ ID NO: 10 (T2G16T2). According to another embodiment, the increased IgG reactivity is of at least one oligonucleotide antigen selected from the group consisting of SEQ ID NO: 1, 3-5, 8-41.

In certain embodiments, the increased IgM and IgG reactivity is of at least one oligonucleotide antigen selected from the group consisting of G1T16 (SEQ ID NO: 42), CCATAATTGCAAACGTTCTG (SEQ ID NO: 1), G1T16G1 (SEQ ID NO: 5), CCATAATTGCAAAGCTTCTG (SEQ ID NO: 3), A20 (SEQ ID NO: 22) and T20 (SEQ ID NO: 8). In certain embodiments, the increased IgM reactivity is of at least one oligonucleotide antigen selected from the group consisting of T16G2 (SEQ ID NO: 28) and T16G1 (SEQ ID NO: 7). Each possibility represents a separate embodiment of the invention.

According to another embodiment, the increased IgM reactivity is of at least one oligonucleotide antigen selected from the group consisting of SEQ ID NOs: 42, 7, 5, 28, 8, 1, 3 and 22. According to another embodiment, the increased IgG reactivity is of at least one oligonucleotide antigen selected from the group consisting of SEQ ID NO: SEQ ID NOs: 42, 7, 5, 28, 8, 1, 3 and 22. Each possibility represents a separate embodiment of the present invention.

According to another embodiment, the method further comprises determining the reactivity of the sample to dsDNA and/or ssDNA. In certain embodiments, the subject is positive for antibodies to dsDNA. In other certain embodiments, the subject is positive for antibodies to ssDNA. In certain embodiments, the subject is negative for antibodies to dsDNA. In other certain embodiments, the subject is negative for antibodies to ssDNA. However, as noted in the background section, the clinical value of anti-dsDNA antibodies largely depends on the assay principle and analytical variables of the methods used to quantitate and immunologically characterize them.

It should be understood that in order to perform the methods of the present invention, samples obtained or derived from subjects must comprise antibodies produced by the subject himself. Therefore, samples may be obtained or derived from any tissue, organ or liquid naturally comprising at least a subset of the subject's antibodies. In certain embodiments, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. Methods for obtaining and isolating appropriate samples are well within the purview of the skilled artisan.

According to certain embodiments of the methods of the present invention, the control is selected from the group consisting of a sample from at least one healthy individual, a panel of control samples from a set of healthy individuals, and a stored set of data from healthy individuals. Each possibility represents a separate embodiment of the invention. Typically, a healthy individual is a subject not afflicted with SLE (or any other form of lupus). In another embodiment, a healthy individual is a subject not afflicted with any autoimmune disease (e.g., scleroderma).

In particular embodiments, the significant difference is determined using a cutoff of a positive predictive value (PPV) of at least 85%, preferably at least 90%. Determining a PPV for a selected marker (e.g., an antigen) is well known to the ordinarily skilled artisan and is exemplified in the methods described below. Typically, positivity for an antigen is determined if it detected above 10% of the subjects in a specific study subgroup using a selected cutoff value, such as PPV ≥90%. For example, antigen i is determined to specifically characterize group A if it detected at least 10% of the subjects in group A with a PPV ≥90% when compared to a different test group B. Subjects in group A that are above the cutoff of PPV ≥90% for antigen i are considered to be positive for antigen i.

An antibody "directed to" an antigen, as used herein is an antibody which is capable of specific binding to the antigen. Determining the levels of antibodies directed to a plurality of antigens includes measuring the level of each antibody in the sample, wherein each antibody is directed to a specific oligonucleotide antigen of the invention. This step is typically performed using an immunoassay, as detailed herein.

In other embodiments, determining the reactivity of antibodies in the sample to the at least one antigen (and the levels of each one of the tested antibodies in the sample) is performed by a process comprising contacting the sample, under conditions such that a specific antigen-antibody complex may be formed, with at least one antigen (or when a plurality of antigens is used, to an antigen probe set comprising the plurality of antigens), and quantifying the amount of antigen-antibody complex formed for each antigen probe. The amount of antigen-antibody complex is indicative of the level of the tested antibody in the sample (or the reactivity of the sample with the antigen).

In another embodiment the method comprises determining the reactivity of at least one IgG antibody and at least one IgM antibody in the sample to the plurality of antigens. In another embodiment, the method comprises determining the reactivity of a plurality of IgG antibodies and at least one IgM antibody in the sample to the plurality of antigens. In another embodiment, the method comprises determining the reactivity of at least one IgG antibody and a plurality of IgM antibodies in the sample to the plurality of antigens. According to another embodiment, the method comprises determining the reactivity of antibodies in the sample to a plurality of oligonucleotide antigens.

Typically, determining the reactivity of antibodies in the sample to at least one antigen is performed using an immunoassay. Advantageously, when a plurality of antigens is used, the plurality of antigens may be used in the form of an antigen array.

Antigen Probes and Antigen Probe Sets

According to further embodiments, the invention provides antigen probes and antigen probe sets useful for diagnosing SLE, as detailed herein.

The invention further provides a plurality of antigens also referred to herein as antigen probe sets. These antigen probe sets comprise a plurality of antigens which are reactive specifically with the sera of subjects having SLE. According to the principles of the invention, the plurality of antigens may advantageously be used in the form of an antigen array. According to some embodiments the antigen array is conveniently arranged in the form of an antigen chip.

A "probe" as used herein means any compound capable of specific binding to a component. According to one aspect, the present invention provides an antigen probe set comprising a plurality of oligonucleotide antigens selected from the group consisting of: SEQ ID NO:1-67 or any combinations thereof. According to certain embodiments, the antigen probe set comprises a subset of the antigens of the present invention. In a particular embodiment, the subset of antigen consists of: SEQ ID NO: 1-10. In another particular embodiment, the subset of antigen consists of: SEQ ID NO: 1, 3-5 and 8-41. In another embodiment, the subset of antigen consists of: SEQ ID NO: 1, 2, 3, 5, 11 and 12. In yet another particular embodiment, the subset of antigen consists of: SEQ ID NO: 8, 15, 22 and 36. In certain embodiment, the subset of antigen consists of: SEQ ID NO: 42, 7, 5, 28, 8, 1, 3 and 22.

According to another embodiment, the methods of the present invention comprise determining the reactivity of antibodies in the sample to at least one oligonucleotide antigen selected from the group consisting of SEQ ID NO: 42, SEQ ID NO: 7, SEQ ID NO: 5, SEQ ID NO: 28, SEQ ID NO: 8, SEQ ID NO: 1, SEQ ID NO: 3, and SEQ ID NO: 22; and to at least one additional oligonucleotide antigen selected from the group consisting of SEQ ID NOs: 1, 3, 5, 7, 8, 10, 17, 18, 22, 28, 34, 36, 38, 41, 42, 43, 44, 65, 66 and 67. Each possibility represents a separate embodiment of the invention.

According to another embodiment, the methods of the present invention comprise determining the reactivity of antibodies in the sample to at least two oligonucleotide antigens selected from the group consisting of SEQ ID NO: 42, SEQ ID NO: 7, SEQ ID NO: 5, SEQ ID NO: 28, SEQ ID NO: 8, SEQ ID NO: 1, SEQ ID NO: 3, and SEQ ID NO: 22. Each possibility represents a separate embodiment of the invention.

The reactivity of antibodies to the plurality of antigens of the invention may be determined according to techniques known in the art.

Preferably, the plurality of antigens of the methods and kits of the invention comprises a set of the antigens as disclosed herein. Yet in other embodiments, the plurality of antigens (or the antigen probe set) comprises or consists of a subset thereof, e.g. 3, 4, 5, 6, 7, 8, 9, 10, 11, 12, 13, 14, 15, 16, 17, 18, 19, 20, 21, 22, 23, 24, 25 ,26, 27, 28, 29, 30, 31, 32, 33,34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 or 67 different antigens, each selected from the antigens of the present invention, wherein each possibility represents a separate embodiment of the invention. Such subsets may be selected so as to result in optimal sensitivity and/or specificity of the diagnostic assay.

Antigen probes to be used in the assays of the invention may be synthesized using methods well known in the art.

It should be noted, that the invention utilizes antigen probes as well as homologs, fragments and derivatives thereof, as long as these homologs, fragments and derivatives are immunologically cross-reactive with these antigen probes. The term "immunologically cross-reactive" as used herein refers to two or more antigens that are specifically bound by the same antibody. The term "homolog" as used herein refers to an oligonucleotide having at least 80%, at least 85% or at least 90% identity to the antigen's nucleic acid sequence. Cross-reactivity can be determined by any of a number of immunoassay techniques, such as a competition assay (measuring the ability of a test antigen to competitively inhibit the binding of an antibody to its known antigen).

The term "fragment" as used herein refers to a portion of an oligonucleotide, or oligonucleotide analog which remains immunologically cross-reactive with the antigen probes, e.g., to immunospecifically recognize the target antigen. The fragment may have the length of about 80%, about 85%, about 90% or about 95% of the respective antigen.

According to another aspect, the present invention provides an antigen probe set comprising a plurality of oligonucleotide antigen probes selected from the group consisting of SEQ ID NOs: 1, 3, 5, 7, 8, 10, 17, 18, 22, 28, 34, 36, 38, 41, 42, 43, 44, 65, 66 and 67.

According to another related aspect, the present invention provides an antigen probe set comprising at least one oligonucleotide antigen probe selected from the group consisting of SEQ ID NOs: 1, 3, 5, 7, 8, 10, 17, 18, 22, 28, 34, 36, 38, 41, 42, 43, 44, 65, 66 and 67.

According to another aspect, the present invention provides an article of manufacture comprising the at least one of the antigen probe sets described above.

In certain embodiments, the article of manufacture is in the form of an antigen probe array or in the form of an antigen chip or in the form of a dipstick or in the form of a lateral flow test or any other platform known to those skilled in the art. An "antigen probe array" generally refers to a plurality of antigen probes, either mixed in a single container or arranges in to or more containers. An "antigen chip" generally refers to a substantially two dimensional surface, onto which a plurality of antigens are attached or adhered. A "dipstick" generally refers to an object, onto which a plurality of antigens are attached or adhered, which is dipped into a liquid to perform a chemical test or to provide a measure of quantity found in the liquid. A "lateral flow test" generally refers to devices intended to detect the presence (or absence) of a target analyte in sample (matrix) without the need for specialized and costly equipment. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use. For example, the aforementioned means may include reagents, detectable labels and/or containers which may be used for measuring specific binding of antibodies to the antigen probes of the invention. "Means" as used herein may also refer to devices, reagents and chemicals, such as vials, buffers and written protocols or instructions, used to perform biological or chemical assays.

According to another aspect, there is provided use of the at least one oligonucleotide antigen selected from the group consisting of: SEQ ID NOs: 1, 3, 5, 7, 8, 10, 17, 18, 22, 28, 34, 36, 38, 41, 42, 43, 44, 65, 66 and 67, for the preparation of a diagnostic kit for diagnosing SLE in a subject. The diagnostic kit is, in some embodiments, useful for determining the reactivity of antibodies in a sample, thereby determining the reactivity pattern of the sample to the at least one oligonucleotide antigen. In some embodiments, a significant difference (e.g., increase) between the reactivity pattern of the sample compared to a reactivity pattern of a control sample is an indication for SLE.

In other embodiments, the plurality of antigens comprised in the antigen probe set comprises or consists up to 50, 55, 60, 70, 80, 90 or 100 different antigens. In other embodiments, the plurality of antigens comprised in the antigen probe set comprises or consists at least 50, 100, 150, 200 or 500 different antigens.

In other aspects, there are provided nucleic-acid vectors comprising the oligonucleotides of the invention and host cells containing them. These nucleic acids, vectors and host cells are readily produced by recombinant methods known in the art. A poly-nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to perform the methods of the present invention.

According to the invention, the kits comprise a plurality of antigens also referred to herein as antigen probe sets. These antigen probe sets comprising a plurality of antigens are reactive specifically with the sera of subjects having SLE. In some embodiments, the antigen probe sets can differentiate between sera of subjects having SLE and subject having scleroderma. According to the principles of the invention, the plurality of antigens may advantageously be used in the form of an antigen array. According to some embodiments the antigen array is conveniently arranged in the form of an antigen chip.

In other embodiments, the kit may further comprise means for determining the reactivity of antibodies in a sample to the plurality of antigens. For example, the kit may contain reagents, detectable labels and/or containers which may be used for measuring specific binding of antibodies to the antigen probes of the invention. In a particular embodiment, the kit is in the form of an antigen array.

In some embodiments, the kit comprises means for comparing reactivity patterns of antibodies in different samples to the plurality of antigens. In other embodiments, the kit may further comprise negative and/or positive control samples. For example, a negative control sample may contain a sample from at least one healthy individual (e.g., an individual not-afflicted with SLE). A positive control may contain a sample from at least one individual afflicted with SLE, or a subtype of SLE which is being diagnosed. Other non-limiting examples are a panel of control samples from a set of healthy individuals or diseased individuals, or a stored set of data from control individuals.

Antibodies, Samples and Immunoassays

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows: (i) Fv, defined as a genetically engineered fragment consisting of the variable region of the light chain and the variable region of the heavy chain expressed as two chains; (ii) single-chain Fv ("scFv"), a genetically engineered single-chain molecule including the variable region of the light chain and the variable region of the heavy chain, linked by a suitable polypeptide linker; (iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof: (iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" is a peptide which is capable of specifically binding an antibody.

In another embodiment, detection of the capacity of an antibody to specifically bind an antigen probe may be performed by quantifying specific antigen-antibody complex formation. The term "specifically bind" as used herein means that the binding of an antibody to a specific antigen probe is not affected by the presence of non-related molecules.

In certain embodiments, the method of the present invention is performed by determining the capacity of an antigen of the invention to specifically bind antibodies of the IgG isotype, or, in other embodiments, antibodies of the IgM, isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. CSF, urine and saliva samples.

Numerous well known fluid collection methods can be utilized to collect the biological sample from the subject in order to perform the methods of the invention.

In accordance with the present invention, any suitable immunoassay can be used with the subject oligonucleotides. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum of the subject so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe.

In various embodiments, the method of the present invention further comprises diluting the sample before performing the determining step. In one embodiment, the sample is diluted 1:2, for instance, using PBS. In another embodiment, the sample is diluted 1:4, 1:6, 1:8, 1:15, 1:20, 1:50, or preferably 1:10. Each possibility represents a separate embodiment of the present invention. In another embodiment, the sample is diluted in the range of times 2-times 10. In another embodiment, the sample is diluted in the range of times 4-times 10. In another embodiment, the sample is diluted in the range of times 6-times 10. In another embodiment, the sample is diluted in the range of times 8-times 10.

The Antigen Chip

Antigen microarrays are used for the high-throughput characterization of the immune response (Robinson et al., 2002, Nat Med 8, 295-301), and have been used to analyze immune responses in vaccination and in autoimmune disorders (Robinson et al., 2002; Robinson et al., 2003, Nat Biotechnol. 21, 1033-9; Quintana et al., 2004; Kanter et al., 2006, Nat Med 12, 138-43). It has been hypothesized, that patterns of multiple reactivities may be more revealing than single antigen-antibody relationships (Quintana et al., 2006, Lupus 15, 428-30) as shown in previous analyses of autoimmune repertoires of mice (Quintana et al., 2004; Quintana et al., 2001, J Autoimmun 17, 191-7) and humans (Merbl et al., 2007, J Clin Invest 117, 712-8; Quintana et al., 2003, J Autoimmun 21, 65-75) in health and disease. Thus, autoantibody repertoires have the potential to provide both new insights into the pathogenesis of the disease and to serve as immune biomarkers (Cohen, 2007, Nat Rev Immunol. 7, 569-74) of the disease process.

According to some aspects the methods of the present invention may be practiced using antigen arrays as disclosed in WO 02/08755 and U.S. 2005/0260770 to some of the inventors of the present invention, the contents of which are incorporated herein by reference. WO 02/08755 is directed to a system and an article of manufacture for clustering and thereby identifying predefined antigens reactive with undetermined immunoglobulins of sera derived from patient subjects in need of diagnosis of disease or monitoring of treatment. Further disclosed are diagnostic methods, and systems useful in these methods, employing the step of clustering a subset of antigens of a plurality of antigens, the subset of antigens being reactive with a plurality of antibodies being derived from a plurality of patients, and associating or disassociating the antibodies of a subject with the resulting cluster.

U.S. Pat. App. Pub. No. 2005/0260770 to some of the inventors of the present invention discloses an antigen array system and diagnostic uses thereof. The application provides a method of diagnosing an immune disease, particularly diabetes type 1, or a predisposition thereto in a subject, comprising determining a capacity of immunoglobulins of the subject to specifically bind each antigen probe of an antigen probe set. The teachings of the disclosures are incorporated in their entirety as if fully set forth herein.

In other embodiments, various other immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, electronic, magnetic detecting and any other system that allows quantitative measurement of antigen-antibody binding.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. First, the glass surface is activated by a chemical treatment that leaves a layer of reactive groups such as epoxy groups on the surface, which bind covalently any molecule containing free amine or thiol groups. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

According to additional embodiments, the antigen probe set comprises at least 100, at least 150, at least 200 or more antigens, including one or a plurality of the antigens provided by the present invention. According to additional embodiments, the antigen probe set comprises at least 100, at least 150, at least 200 or more oligonucleotide antigens, including one or a plurality of the oligonucleotide antigens provided by the present invention.

In addition to antigen probes of the invention, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements. Normalization control probes can be bound to various addressable locations on the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgM isotype, the antibody ligand is preferably an antibody capable of specifically binding to the Fc region of IgM antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, Dy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g. 1:10 dilution), the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Data Analysis

Advantageously, the methods of the invention may employ the use of learning and pattern recognition analyzers, clustering algorithms and the like, in order to discriminate between reactivity patterns of healthy control subjects to those of patients having SLE. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from control subjects which are not afflicted with SLE or patients afflicted with SLE, respectively) using such algorithms and/or analyzers. The difference may also be measured by comparing the reactivity pattern of the test sample to a predetermined classification rule obtained in such manner.

In some embodiments, the methods of the invention may employ the use of learning and pattern recognition analyzers, clustering algorithms and the like, in order to discriminate between reactivity patterns of subjects having a subtype of SLE to control subjects. For example, the methods may include determining the reactivity of antibodies in a test sample to a plurality of antigens, and comparing the resulting pattern to the reactivity patterns of negative and positive control samples using such algorithms and/or analyzers.

Thus, in another embodiment, a significant difference between the reactivity pattern of a test sample compared to a reactivity pattern of a control sample, wherein the difference is computed using a learning and pattern recognition algorithm, indicates that the subject is afflicted with SLE. For example, the algorithm may include, without limitation, supervised or non-supervised classifiers including statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor, artificial neural networks, coupled two-way clustering algorithms, multi-layer perceptrons (MLP), generalized regression neural network (GRNN), fuzzy inference systems (FIS), self-organizing map (SOM), genetic algorithms (GAS), neuro-fuzzy systems (NFS), adaptive resonance theory (ART).

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Diagnostic Methods

As used herein the term "diagnosing" or "diagnosis" refers to the process of identifying a medical condition or disease (e.g., SLE) by its signs, symptoms, and in particular from the results of various diagnostic procedures, including e.g. detecting the reactivity of antibodies in a biological sample (e.g. serum) obtained from an individual, to one or more oligonucleotide antigens. Furthermore, as used herein the term "diagnosing" or "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis. The "accuracy" of a diagnostic assay is the proximity of measurement results to the true value. The "p value" of a diagnostic assay is the probability of obtaining the observed sample results (or a more extreme result) when the null hypothesis is actually true.

In certain embodiments, the use of an antigen probe set provided by the present invention, or an antigen probe array provided by the present invention, results in an antibody reactivity profile which is SLE-indicative (p value≤1.00E-08), sensitive (≥0.600), specific (≥0.700) and accurate (≥0.600). In certain embodiments, the use results in an antibody reactivity profile which is more SLE-indicative (p value≤1.00E-10), sensitive (≥0.700), specific (≥0.800) and accurate (≥0.700). In certain embodiments, the use results in an antibody reactivity profile which is even more SLE-indicative (p value≤1.00E-12), sensitive (≥0.800), specific (≥0.900) and accurate (≥0.800). In certain embodiments, the use results in an antibody reactivity profile which is yet even more SLE-indicative (p value≤1.00E-14), sensitive (≥0.900), specific (≥0.950) and accurate (≥0.900). In certain embodiments, the use results in an antibody reactivity profile which highly SLE-indicative (p value≤1.00E-16), sensitive (≥0.950), specific (≥0.990) and accurate (≥0.950). Each possibility represents a separate embodiment of the invention.

In certain embodiments, the oligonucleotide antigens provided by the present invention, or the oligonucleotide antigen patterns provided by the present invention, are SLE-indicative (p value ≤1.87E-08), sensitive (≥0.609), specific (≥0.769) and accurate (>0.687). In certain embodiments, the oligonucleotide antigens provided by the present invention, or the oligonucleotide antigen patterns provided by the present invention, are advantageously SLE-indicative (p value≤2.81E-12), sensitive (≥0.657), specific (≥0.798) and accurate (≥0.725). In certain embodiments, the oligonucleotide antigens provided by the present invention, or the oligonucleotide antigen patterns provided by the present invention, are further advantageously SLE-indicative (p value≤8.00E-14), sensitive (≥0.663), specific (≥0.814) and accurate (≥0.738).

In another embodiment, the methods may result in determining a level of SLE disease activity. In a further embodiment, the methods may result in providing the comparison to an entity for monitoring SLE disease activity. In these embodiments, the methods can be used, for example, to differentiate between subjects with active disease and those with non-active disease.

In some embodiments, the methods of the invention are useful in diagnosing systemic lupus erythematosus (SLE) or lupus. "Lupus" as used herein is an autoimmune disease or disorder involving antibodies that attack connective tissue. According to some embodiments, the invention provides diagnostic methods useful for the detection of SLE.

In one embodiment, the subject being diagnosed according to the methods of the invention is symptomatic. In other embodiments, the subject is asymptomatic. In certain embodiments, the subject is not or was not receiving an immunosuppressive drug or an immunosuppressive treatment.

The diagnostic procedure can be performed in vivo or in vitro, preferably in vitro. In certain embodiments of the methods of the present invention, the diagnostic procedure is performed by non-invasive means or methods.

Systemic Lupus Erythematosus (SLE)

The 1982 American College of Rheumatology (ACR) criteria describes features necessary to diagnose SLE. The presence of as few as 4 of the 11 criteria yields a sensitivity of 85% and a specificity of 95% for SLE. Patients with SLE may present with any combination of clinical features and serologic evidence of lupus. The ACR's criteria are (1) Serositis (pleurisy, pericarditis on examination or diagnostic ECG or imaging), (2) Oral ulcers (oral or nasopharyngeal, usually painless; palate is most specific), (3) Arthritis (non-erosive, two or more peripheral joints with tenderness or swelling), (4) Photosensitivity (unusual skin reaction to light exposure), (5) Blood disorders (leukopenia (<4×10$^3$ cells/μL on more than one occasion), lymphopenia (<1500 cells/μL on more than one occasion), thrombocytopenia (<100 ×10$^3$ cells/µL in the absence of offending medications), hemolytic anemia), (6) Renal involvement (proteinuria (>0.5 g/d or 3+ positive on dipstick testing) or cellular casts), (7) ANAs (higher titers generally more specific (>1:160); must be in the absence of medications associated with drug-induced lupus), (8) Immunologic phenomena (dsDNA; anti-Smith (Sm) antibodies; antiphospholipid antibodies (anticardiolipin immunoglobulin G [IgG] or immunoglobulin M [IgM] or lupus anticoagulant); biologic false-positive serologic test results for syphilis, lupus erythematosus (LE) cells (omitted in 1997)), (9) Neurologic disorder (seizures or psychosis in the absence of other causes), (10) Malar rash (fixed erythema over the cheeks and nasal bridge, flat or raised), and (11) Discoid rash (erythematous raised-rimmed lesions with keratotic scaling and follicular plugging, often scarring).

The Systemic Lupus Collaborating Clinics (SLICC) recently revised and validated the American College of Rheumatology (ACR) SLE classification criteria in order to improve clinical relevance, meet stringent methodology requirements and incorporate new knowledge in SLE immunology (Petri et al., Arthritis and Rheumatism, 2012, Vol. 64, pages 2677-2686). Seventeen criteria were identified, including 11 clinical criteria and 6 immunological criteria. The SLICC criteria for SLE classification requires fulfillment of at least four criteria, with at least one clinical criterion and one immunologic criterion, or lupus nephritis as the sole clinical criterion in the presence of ANA or anti-dsDNA antibodies.

Two of the most commonly used instruments for SLE diagnosis are the Systemic Lupus Erythematosus Disease Activity Index (SLEDAI) and the Systemic Lupus Activity Measure (SLAM).

The SLEDAI is an index that measures disease activity by weighting the importance of each organ system involved. The SLEDAI includes 24 items, representing nine organ systems. The variables are obtained by history, physical examination and laboratory assessment. Each item is weighted from 1 to 8 based on the significance of the organ involved. For example, mouth ulcers are scored as 2, while seizures are scored as 8. The laboratory parameters that are included in the SLEDAI include white blood cell count, platelet count, urinalysis, serum C3, C4 and anti-dsDNA. The total maximum score is 105.

The SLAM includes 32 items representing 11 organ systems. The items are scored not only as present/absent, but graded on a scale of 1 to 3 based on severity. The total possible score for the SLAM is 86. Both the SLEDAI and the SLAM have been shown to be valid, reliable, and sensitive to change over time (Liang et al. 1989, Arth Rheum 32:1107-18), and are widely used in research protocols and clinical trials. These indices are particularly useful for examining the value of newly proposed serologic or inflammatory markers of disease activity in SLE.

Despite the obvious utility of these instruments, there are some drawbacks. First, there is not always complete agreement between the SLAM and the SLEDAI in the same set of patients. There are several possible reasons for these discrepancies. Unlike the SLEDAI, the SLAM includes constitutional symptoms such as fatigue and fever, which may or may not be considered attributable to active SLE; this activity index relies on physician interpretation. In addition, the SLEDAI does not capture mild degrees of activity in some organ systems and does not have descriptors for several types of activity, such as hemolytic anemia.

Scleroderma (or systemic sclerosis) is an autoimmune disease that is characterized by endothelial cell damage, fibroblast activation, extracellular matrix (ECM) accumulation and abnormal angiogenesis that carries a high rate of morbidity and mortality. One of the major causes of mortality is fibrosis of lung tissue (interstitial lung disease) and severe pulmonary hypertension. The pathogenesis of scleroderma remains unclear, but is thought to involve an autoimmune response against target organs with early production of auto-antibodies and inflammatory mononuclear cell infiltrates followed by loss of organ function and fibrosis. Principal target organs are the skin, the gastrointestinal tract, the lungs and kidneys, although other organs are also frequently involved. Widespread scleroderma can occur with other autoimmune diseases, including SLE.

The following examples are presented in order to more fully illustrate some embodiments of the invention. They should, in no way be construed, however, as limiting the broad scope of the invention.

EXAMPLES

Materials and Methods

Human Subjects

The study was approved by the Institutional Review Boards of each participating clinical unit; informed consent was obtained from all participants. In an initial study, sera derived from blood samples obtained from 22 healthy subjects, 18 Pemphigus Vulgaris (PV) patients, 15 Scleroderma and Systemic Sclerosis (SSc) patients, and 34 Systemic Lupus Erythematosus (SLE) patients were tested using an antigen microarray that included A20 (SEQ ID NO: 22), C20 (SEQ ID NO: 15), G20 (SEQ ID NO: 43) and T20 (SEQ ID NO: 8) single-stranded oligonucleotides. In a follow-up study, sera samples obtained from 23 healthy subjects, 24 SSc patients, and 49 SLE patients were tested using an antigen microarray that included 58 single-stranded oligonucleotides. Overall, 60 SLE patients, 26 SSc patients, 18 PV patients, and 31 healthy subjects were tested. SLE and SSc patients were diagnosed according to clinically accepted criteria (Criteria published by EM Tan et al. Arthritis Rheum 1982; 25:1271, updated by MC Hochberg, Arthritis Rheum 1997;40:1725; Preliminary criteria for the classification of systemic sclerosis (scleroderma). Subcommittee for scleroderma criteria of the American Rheumatism Association Diagnostic and Therapeutic Criteria Committee. Arthritis Rheum. 1980;23(5):581-90). The diagnosis of PV was based upon clinical features and laboratory tests: suprabasal separation on histology of skin lesions, positive direct and indirect immunofluorescence microscopy, and/or ELISA detection of anti-desmoglein Abs (Zagorodniuk I, et al. Int J Dermatol. 2005 Jul; 44(7):541-4).

Blood samples and clinical data were collected from patients arriving at the Rheumatology and Nephrology Units at Rabin Medical Center, PetachTikva, Israel; the Rheumatology Unit and the Hematology Department of the Sheba Medical Center, Israel; the Department of Dermatology, Tel Aviv Sourasky Medical Center; and the Dipartimento di Scienze Mediche e Chirurgiche, Sezione di Clinica Medica, Polo Didattico, Ancona, Italy. Inclusion criteria were ACR criteria score of >3 at time of diagnosis. Healthy control samples were obtained under study protocols approved by the Institutional Review Boards of each participating clinical unit; informed consent was obtained from all participants.

Samples were also obtained from 83 healthy subjects of an average age of 35, including 47 Africans, 15 White & Caucasian, 4 Indian/Asian/middle eastern and 17 Hispanic; and 77 SLE patients, of the same average age, including 47 Africans, 6 White & Caucasian, 17 Hispanic and 1 of another descent.

Antigens and Serum Testing

In a follow-up study, 58 different oligonucleotides, as well as double and single stranded DNA, in various lengths (104 different preparations overall), were spotted on epoxy-activated glass substrates (ArrayIt SuperEpoxi microarray substrate slides, Sunnyvale, Calif.). The oligonucleotides were purchased from SBS Genetech Co., Ltd. (Shanghai, China). The microarrays were then blocked for 1 hour at 37° with 1% bovine serum albumin Test serum samples in 1% Bovine Serum Albumin (BSA) blocking buffer (1:10 dilution) were incubated under a coverslip for 1 hour at 37°. The arrays were then washed and incubated for 1 hour at 37° with a 1:500 dilution of two detection antibodies, mixed together: a goat anti-human IgG Cy3-conjugated antibody, and a goat anti-human IgM Cy5-conjugated antibody (both purchased from Jackson ImmunoResearch Laboratories Inc., West Grove, Pa.). Image acquisition was performed by laser (Agilent Technologies, Santa Clara, Calif.) and the results were analyzed using Quantarray software (Packard BioChip Technologies, Billerica, Mass.). The quantitative range of signal intensity of binding to each antigen spot was 0-65, 000; this range of detection made it possible to obtain reliable data at a 1:10 dilution of test serum samples.

Alternatively, oligonucleotide antigens and double and single stranded DNA in various chain lengths were spotted on epoxyhexyltriethoxysilane (EHTES) activated slides. The microarrays were then blocked for 1 hour at room temperature with 1% casein. Test serum samples in 1% casein blocking buffer (1:20 dilution) were incubated under a coverslip for 1 hour at 37°. The arrays were then washed and incubated for 1 hour at 37° with a 1:500 dilution of two detection antibodies, mixed together: a goat anti-human IgG Cy3-conjugated antibody, and a goat anti-human IgM AF647-conjugated antibody (both purchased from Jackson ImmunoResearch Laboratories Inc., West Grove, Pa.). Image acquisition was performed by laser at two wavelengths 530nm and 630 nm (Agilent Technologies, Santa Clara, Calif.) and the results were analyzed using Genepix Pro 7.0 software with default settings. The quantitative range of signal intensity of binding to each antigen spot was 0-65,000; this range of detection made it possible to obtain reliable data at a 1:20 dilution of test samples.

Image Analysis and Data Processing

Each spot's intensity is represented by its pixels' mean after subtraction of its local background median, followed by Log2 transform. Negative spots (following background subtraction) are imputed with background-like intensity. The foreground and background intensities of multiple spots of each antigen were averaged, and the difference between the foreground and the background was calculated. The resulting value was taken as the antigen reactivity of the antibodies binding to that spotted antigen. All antigens showed meaningful reactivity in a significant number of slides; thus no antigen was excluded.

Statistical Analysis of Antibody Results

Antigens whose reactivity was higher or lower in a specific study subgroup compared to other subgroups were identified. Antigens that allowed for setting a classification threshold such as positive predictive value (PPV) ≥90% and sensitivity ≥20% were achieved and determined to significantly characterize a specific subgroup. SLE patients were marked positive for dsDNA if their reactivity to dsDNA passed this requirement. For added restriction, only antigens whose p value for a two sided t-test (after Benjamini-Hochberg correction for multiple hypothesis) was smaller than 0.05 were selected.

Example 1

Antibodies' Binding to Homo-nucleotide 20-mers

Sera samples from healthy subjects, PV, SSc and SLE patients were tested for binding of serum IgG and IgM antibodies to four 20-mer homo-nucleotides: G20 (SEQ ID NO: 43), A20 (SEQ ID NO: 22), C20 (SEQ ID NO: 15), and T20 (SEQ ID NO: 8) (FIG. 1). The reactivities were ordered by each subject's reactivity to dsDNA, from left to right. It can be seen that IgG reactivities to G20 (SEQ ID NO: 43) were very high in all subjects, and significantly higher than the very low reactivities to the other oligonucleotides. However, PV patients were found to have significantly lower IgG and IgM reactivities to $G_{20}$ than did SSc patients. Apart from that, no difference was found between the study groups.

IgG reactivities to A20 (SEQ ID NO: 22), C20 (SEQ ID NO: 15), and T20 (SEQ ID NO: 8) in SLE patients correlated with their reactivities to dsDNA; Patients with low reactivities to dsDNA did not manifest reactivities to A20 (SEQ ID NO: 22), C20 (SEQ ID NO: 15), and T20 (SEQ ID NO: 8), but several patients with higher reactivities to dsDNA showed some reactivities to A20 (SEQ ID NO: 22), C20 (SEQ ID NO: 15), and T20 (SEQ ID NO: 8) (FIG. 1). Healthy subjects, SSc and PV patients had very low or no reactivities to A20 (SEQ ID NO: 22), C20 (SEQ ID NO: 15), and T20 (SEQ ID NO: 8).

IgM reactivities to the four homo-nucleotide sequences were more diffuse: some subjects in each group showed high reactivities to G20 (SEQ ID NO: 43), but, in contrast to the IgG reactivities to G20 (SEQ ID NO: 43), some of the sera showed little or no IgM binding to G20 (SEQ ID NO: 43).

To further characterize the antibodies' reactivity against polyG and polyT oligonucleotides, an additional study on 23 healthy subjects, 24 SSc patients, and 49 SLE patients was performed. An extended microarray antigen chip was used. The chip contained 58 oligonucleotides, including polyG and polyT sequences with and without modifications (see below). The SLE patients were divided according to their reactivity to dsDNA in order to see if dsDNA positivity or negativity was associated with antibodies to the synthetic oligonucleotides. The results of the IgM and IgG reactivities to G20 (SEQ ID NO: 43), A20 (SEQ ID NO: 22), C20 (SEQ ID NO: 15), and T20 (SEQ ID NO: 8) of the first study were confirmed. Combining both studies yielded a total of 60 SLE patients, 26 SSc patients, 18 PV patients and 31 healthy subjects who all displayed high IgG reactivities to G20 (SEQ ID NO: 43) and relatively low reactivities to A20 (SEQ ID NO: 22), C20 (SEQ ID NO: 15), and T20 (SEQ ID NO: 8). Mean IgG reactivities to G20 (SEQ ID NO: 43) where significantly higher than the other poly-nucleotides in all the study groups.

Figure 2:
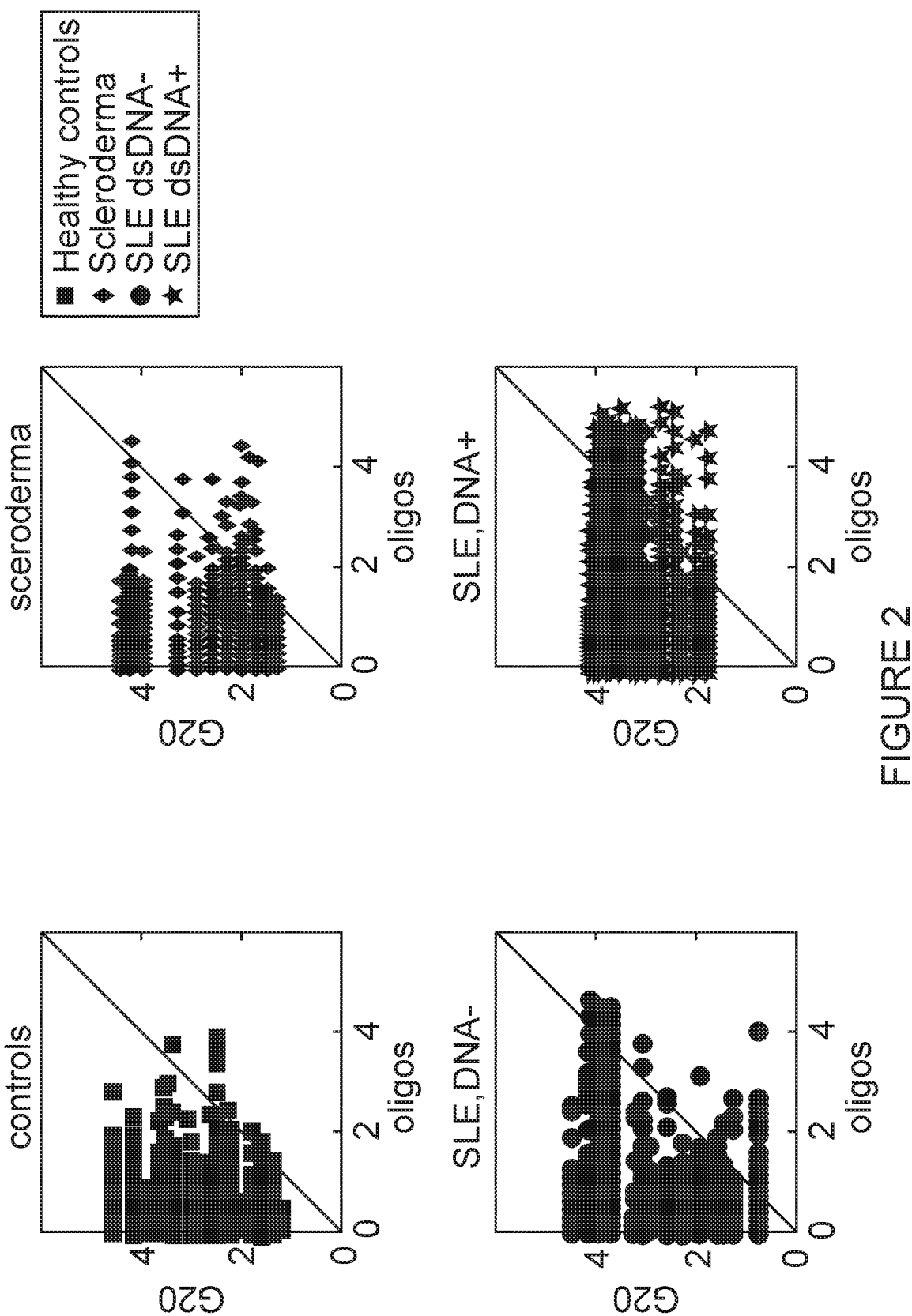
FIG. 2 shows IgG reactivity to G20 (SEQ ID NO: 43) compared to all other oligonucleotides in healthy persons, SSc patients, SLE patients who are negative or positive for dsDNA. Y axis—reactivities for G20 (SEQ ID NO: 43), X axis—reactivities to oligonucleotides. The numbers that appear on both axes are X 10,000.

The IgG reactivities to G20 (SEQ ID NO: 43) were compared to IgG reactivities to the other oligonucleotides and to ssDNA and dsDNA. FIG. 2 shows a scatter plot in which each dot represents the IgG reactivity to G20 (SEQ ID NO: 43) divided by a specific oligonucleotide. Since some of the oligonucleotides and ssDNA and dsDNA were in replicates and mixtures, each subject is represented by 97 spots. Higher reactivity to G20 (SEQ ID NO: 43) compared to a different oligonucleotide would be represented by a dot above the diagonal. Note that out of the 2231 spots of the 23 healthy subjects, only 10 were below the diagonal. This number increases a little for SSc patients and dsDNA-negative SLE patients, and peaks for dsDNA-positive patients (FIG. 2). Nevertheless, the average IgG reactivities to G20 (SEQ ID NO: 43) were significantly higher than IgG reactivities to any other oligonucleotide in all four subgroups tested.

The list of oligonucleotides tested on the antigen chip was as follows: A20 (SEQ ID NO: 22), C20 (SEQ ID NO: 15), T2G16T2 (SEQ ID NO: 10), G2T16G2 (SEQ ID NO: 16), (GA)10 (SEQ ID NO: 44), (GT)10 (SEQ ID NO: 45), G4-7,9,11,14,17,20 (SEQ ID NOs: 46, 37, 13, 17, 34, 47, 41, 36 and 43, respectively), T4-7,9,11,14,17,20 (SEQ ID NOs: 48, 49, 35, 9, 50, 40, 4, 2 and 8, respectively), (CG)2-6,8,10 (SEQ ID NOs: 51, 52, 53 ,54, 29, 55 and 25, respectively), (C*G)2-6,8,10 (*=with C methyl) (SEQ ID NOs: 56, 57, 39, 58, 30, 33 and 26, respectively), T1G16T1 (SEQ ID NO: 20), G16T1 (SEQ ID NO: 18), T1G16 (SEQ ID NO: 38), G16T2 (SEQ ID NO: 12), T2G16 (SEQ ID NO: 24), G1T16G1 (SEQ ID NO: 5), T16G1 (SEQ ID NO: 7), G1T16 (SEQ ID NO: 42), T16G2 (SEQ ID NO: 28), G2T16 (SEQ ID NO: 14), GACGCT (SEQ ID NO: 59), GACGTT (SEQ ID NO: 6), G10GACGCT (SEQ ID NO: 27), G10GACGTT (SEQ ID NO: 60), GAGCCT (SEQ ID NO: 21), GAGCTT (SEQ ID NO: 61), G10GAGCCT (SEQ ID NO: 19), G10GAGCTT (SEQ ID NO: 62), CCCGGA (SEQ ID NO: 63), G10CCCGGA (SEQ ID NO: 32), and TCCATAACGTTGCAACGTTCTG (SEQ ID NO: 64).

Example 2

Figure 3:
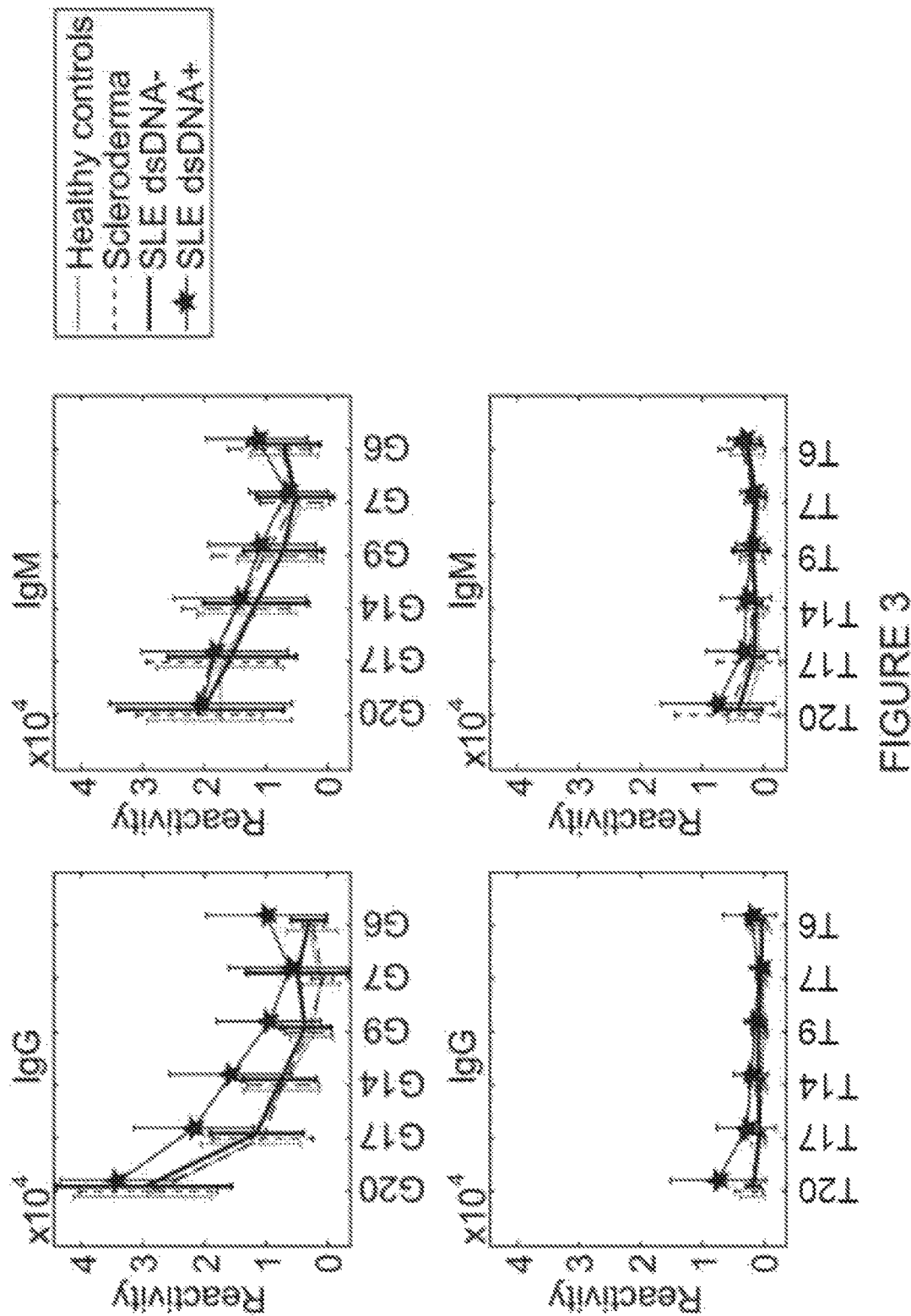
FIG. 3 shows mean IgM and IgG binding to polyG and polyT oligonucleotides as a function of chain length.

Antibody Binding to Poly-G or Poly-T is Related to the Length of the Homo-nucleotide FIG. 3 shows the effect of variable lengths of the nucleotide oligomers on the mean IgG and IgM binding of each tested group to the T or G homo-nucleotides. It can be seen that, except for SLE patients positive for anti-dsDNA who showed reactivities to $T_{20}$, none of the other groups showed appreciable IgG or IgM mean reactivities to any of the poly-T homo-nucleotides. In contrast, mean IgG reactivities to poly-G in all of the sera were high to G20 (SEQ ID NO: 43) and fell significantly as the lengths of the nucleotide chains were reduced to G17 (SEQ ID NO: 36) and below. Surprisingly, SLE patients positive for anti-dsDNA manifested higher mean IgG reactivities to the shorter G polymers than did the other groups.

Mean IgM binding to G20 (SEQ ID NO: 43) was lower than the IgG binding, and IgM binding was also affected by shortening the length of the oligomer. Note that the mean IgM binding of the SLE patients positive to dsDNA did not differ from that of the other groups.

Example 3

The Effects of Adding a Single T to Either the 5' or the 3' Termini of $G_{16}$

Figure 4:
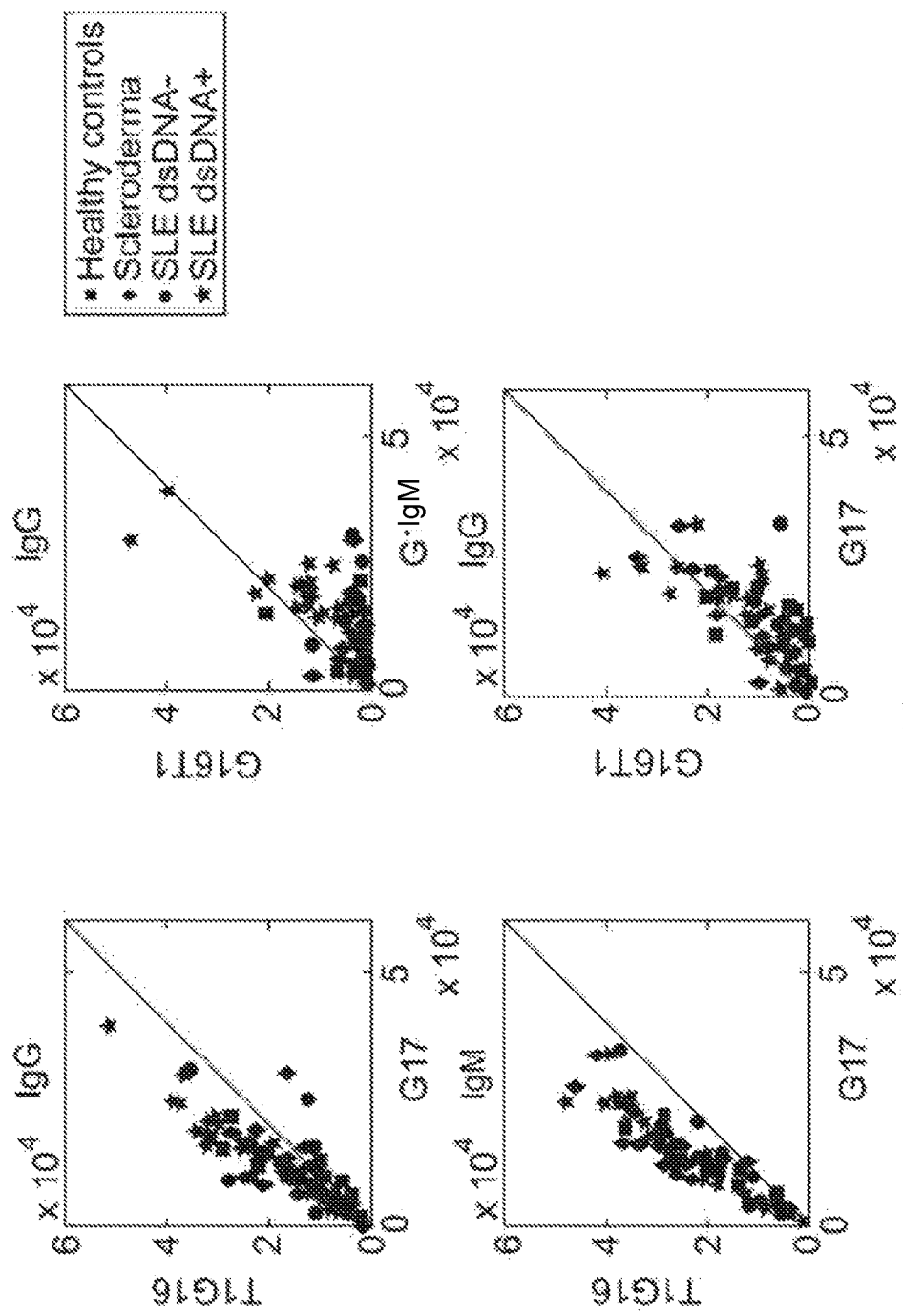
FIG. 4 depicts IgM and IgG reactivities to G17 (SEQ ID NO: 36) oligonucleotide compared to T1G16 (SEQ ID NO: 38) and G16T1 (SEQ ID NO: 18).

The degree of binding of IgG or IgM to G17 (SEQ ID NO: 36) compared to $G_{16}$ to which a single T had been added either at the 5' or 3' end of the G-oligonucleotide chain was tested. FIG. 4 shows the results for individual subjects. It can be seen that both the IgG and IgM binding to T1G16 (SEQ ID NO: 38) was essentially equal to the binding to the G17 (SEQ ID NO: 36) chain, as evident from the diagonal between G17 (SEQ ID NO: 36) and T1G16 (SEQ ID NO: 38). However, the binding of each subject to G16T1 (SEQ ID NO: 18) was considerably less than the binding to G17 (SEQ ID NO: 36); a diagonal relationship was no longer present. Thus, it would appear that the reactivities to poly-G in each of the subject groups was highly influenced by the addition of a single T moiety to the 3' end of the poly-G chain but not by the addition of a T to the 5' end of the G chain; the spatial order of the nucleotides would appear to form an antigen structure critical to antibody binding.

Example 4

The Effects of Single G Additions to the Ends of Poly-T Sequences

Figure 5A:
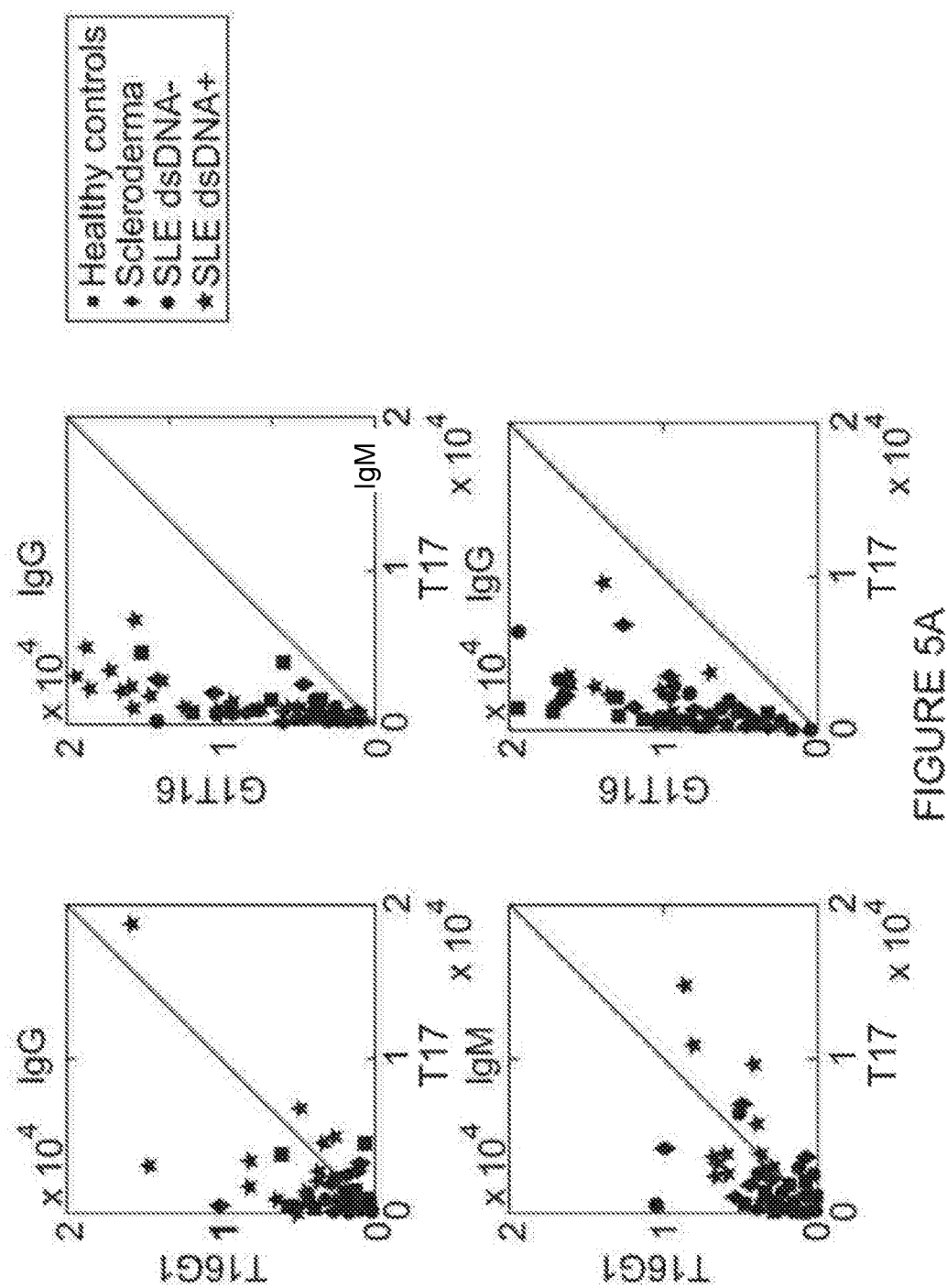
FIGS. 5A-B depict IgM and IgG reactivities to modified $T_{17}$ oligonucleotides G1T16 (SEQ ID NO: 42) and T16G1 (SEQ ID NO: 7) (5A) and G2T16 (SEQ ID NO: 14) and T16G2 (SEQ ID NO: 28) (5B) compared to T17 (SEQ ID NO: 2) reactivities.
Figure 5B:
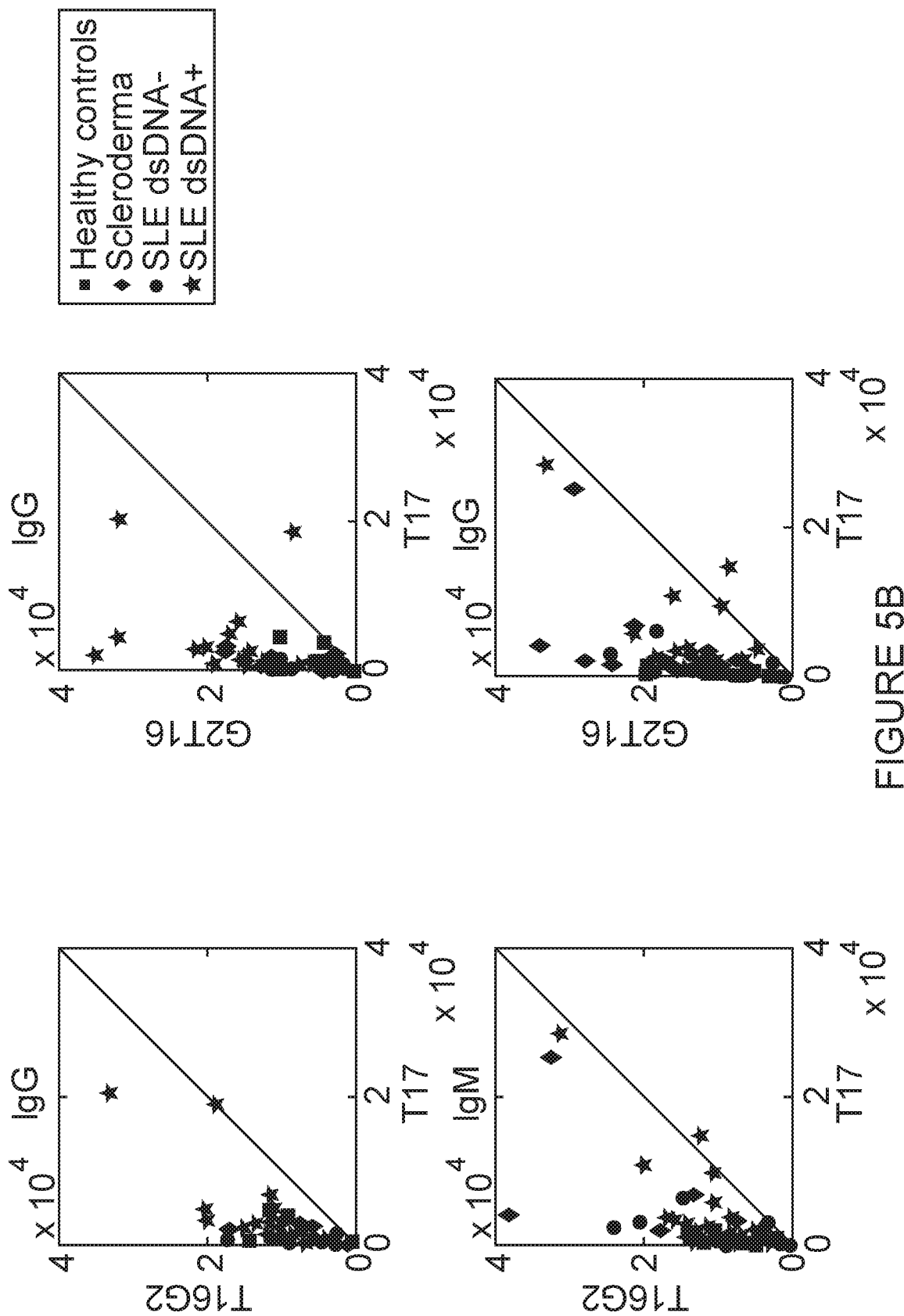

In view of the marked effects of adding a single T to the 3' end of a poly-G chain (Example 3), the effects on IgG or IgM antibody binding by adding a single G to either the 5' or 3' end of a poly-T chain was tested. FIG. 5A shows that although both IgM and IgG reactivities to G1T16 (SEQ ID NO: 42) and to T16G1 (SEQ ID NO: 7) increased in almost all the subjects (most points are above the diagonal), the increases were much more pronounced when the guanine was added to the 5' end. Similarly IgM and IgG reactivities to G2T16 (SEQ ID NO: 14) and T16G2 (SEQ ID NO: 28) were also increased compared to T17 (SEQ ID NO: 2) (FIG. 5B).

In summary, reactivities to poly-T oligonucleotides could be increased significantly by the addition of even a single G to either end of the chain; this was in marked contrast to the inhibition of antibody binding to poly-G by the addition of a single T to the 3' end of the chain.

Example 5

Reactivities to CpG Repeats

IgM reactivities were measured in three subgroups to a 20-mer formed by 10 repetitions of the C-G di-nucleotides, (CG)10 (SEQ ID NO: 25). IgM reactivities to (CG)10 (SEQ ID NO: 25) were high in all but one of the healthy subjects, in all of the SSc patients and in most of the SLE patients. Indeed, a subgroup of SLE patients manifested low IgM reactivities to (CG)10 (SEQ ID NO: 25), a significant difference from the SSc patients (FIG. 6A). A group of SLE patients, mainly those positive for anti-dsDNA, manifested high IgG reactivities to (CG)10 (SEQ ID NO: 25)(FIG. 6B).

Example 6

IgG and IgM Reactivities to dsDNA, ssDNA and Synthetic Oligonucleotides in SLE Patients Compared to Those of Healthy Subjects and SSc Patients Table 1 lists the oligonucleotides with increased or decreased antibody binding in SLE patients compared to healthy controls or SSc patients. A broad spectrum of oligonucleotides was found to bind both IgM and IgG antibodies in SLE patients compared to healthy subjects. IgM and IgG reactivities to dsDNA overlapped; 18 of 23 (78%) SLE patients positive for IgM anti-dsDNA were also positive for IgG anti-dsDNA. Furthermore, the increased IgM and IgG reactivity to the oligonucleotides in the SLE patients overlapped with the IgM and IgG reactivity to dsDNA, respectively. Thus, the subgroup of dsDNA-positive SLE patients shows increased reactivities to oligonucleotides generally, perhaps to a backbone structure, compared to the dsDNA-negative patients.

IgG reactivities as well as IgM reactivities to oligonucleotides were found to be significantly increased in SLE compared to healthy controls and/or SSc patients.

TABLE 1

Antibody reactivities to oligonucleotides in SLE patients compared to healthy controls and SSc patients.

| Oligonucleotides | SEQ ID NO: | Sensitivity(%) for PPV[a] ≥ 90% | |
| --- | --- | --- | --- |
| | | SLE compared to controls | SLE compared to SSc |
| *IgM increase* | | | |
| dsDNA | | 47 | NS[b] |
| CCATAATTGCAAACGTTCTG | 1 | 47 | NS |
| $T_{17}$ | 2 | 45 | NS |
| CCATAATTGCAAAGCTTCTG | 3 | 43 | NS |
| ssDNA | | 39 | NS |
| $T_{14}$ | 4 | 29 | NS |
| $G_1T_{16}G_1$ | 5 | 24 | NS |
| GACGTT | 6 | 24 | NS |
| $T_{16}G_1$ | 7 | 24 | NS |
| $T_{20}$ | 8 | 24 | NS |
| $T_7$ | 9 | 22 | NS |
| $T_2G_{16}T_2$ | 10 | 20 | NS |
| *IgM decrease* | | | |
| $(C*G)_{10}$ | 26 | NS | 29 |
| $(CG)_{10}$ | 25 | NS | 27 |
| *IgG increase* | | | |
| $G_{10}T_{10}$ | 11 | 78 | NS |
| CCATAATTGCAAAGCTTCTG | 3 | 71 | 61 |
| CCATAATTGCAAACGTTCTG | 1 | 69 | 47 |
| ssDNA | | 69 | 39 |
| $G_{16}T_2$ | 12 | 65 | 39 |
| $G_1T_{16}G_1$ | 5 | 65 | 22 |
| dsDNA | | 65 | 63 |
| $G_6$ | 13 | 63 | 47 |
| $G_2T_{16}$ | 14 | 63 | 33 |
| $C_{20}$ | 15 | 61 | 41 |
| $G_2T_{16}G_2$ | 16 | 61 | NS |
| $G_7$ | 17 | 61 | 39 |
| $G_{16}T_1$ | 18 | 59 | 22 |
| $T_2G_{16}T_2$ | 10 | 59 | 47 |
| $G_{10}GAGCCT$ | 19 | 57 | 41 |
| $T_1G_{16}T_1$ | 20 | 57 | 22 |
| GAGCCT | 21 | 51 | NS |
| $A_{20}$ | 22 | 47 | 39 |
| $C_3G_3$ | 23 | 47 | 35 |
| $T_{14}$ | 4 | 47 | NS |

TABLE 1-continued

Antibody reactivities to oligonucleotides in SLE patients compared to healthy controls and SSc patients.

| | | Sensitivity(%) for PPV[a] ≥ 90% | |
|---|---|---|---|
| Oligonucleotides | SEQ ID NO: | SLE compared to controls | SLE compared to SSc |
| $T_2G_{16}$ | 24 | 47 | NS |
| $(CG)_{10}$ | 25 | 45 | 31 |
| $(C*G)_{10}$ | 26 | 45 | 29 |
| $G_{10}GACGCT$ | 27 | 45 | 45 |
| $T_{16}G_2$ | 28 | 45 | 29 |
| $(CG)_6$ | 29 | 43 | 31 |
| $(C*G)_6$ | 30 | 41 | 33 |
| $G_{10}A_{10}$ | 31 | 41 | 47 |
| $G_{10}CCCGGA$ | 32 | 41 | 39 |
| $(C*G)_8$ | 33 | 39 | 31 |
| $T_{20}$ | 8 | 37 | NS |
| $G_9$ | 34 | 35 | 27 |
| $T_6$ | 35 | 35 | NS |
| $G_{17}$ | 36 | 31 | NS |
| $G_5$ | 37 | 31 | 61 |
| $T_1G_{16}$ | 38 | 27 | 27 |
| $(C*G)_4$ | 39 | 24 | 24 |
| $T_{11}$ | 40 | 24 | NS |
| $G_{14}$ | 41 | 20 | NS |
| $T_7$ | 9 | 20 | 20 |

[a]PPV, Positive predictive value; [b]NS, Not significant.

Example 7

IgG and IgM Reactivities to Synthetic Oligonucleotides in SLE Patients Compared to Those of Healthy Subjects Table 2 lists the oligonucleotides with increased or decreased antibody binding in two subgroups of subjects (77 SLE patients compared to 83 healthy controls).

Mean differences in binding of IgM and IgG antibodies from SLE patients compared to healthy controls to a variety of oligonucleotide antigens are presented as mean difference, difference significance (p value), and false discovery rate-corrected p value (used to correct for multiple comparisons), wherein positive values indicate an increase in binding over the level measured in healthy controls (HC) and negative values indicate a decrease in binding over the level measured in HC.

A broad spectrum of oligonucleotides was found to bind more IgM and IgG antibodies in SLE patients compared to healthy subjects. Examples of such oligonucleotide antigens are G1T16 (SEQ ID NO: 42), CCATAATTGCAAACGT-TCTG (SEQ ID NO: 1), G1T16G1 (SEQ ID NO: 5), CCATAATTGCAAAGCTTCTG (SEQ ID NO: 3), A20 (SEQ ID NO: 22) and T20 (SEQ ID NO: 8). Other oligonucleotides were found to bind more IgM or more IgG antibodies in SLE patients compared to healthy subjects. Examples of oligonucleotide antigens found to bind more IgM are T16G2 (SEQ ID NO: 28) T16G1 (SEQ ID NO: 7).

TABLE 2

Reactivities to oligonucleotides in SLE patients compared to controls.

| Antigen | IgM Mean Difference (SLE-HC) | IgM p value | IgM FDR[a] corrected p value | IgM Mean Difference (SLE-HC) | IgG p value | IgG FDR[a] corrected p value |
|---|---|---|---|---|---|---|
| $G_1T_{16}$ | 0.71558 | 5.04E-06 | 3.87E-05 | 2.132 | 9.18E-08 | 4.22E-06 |

TABLE 2-continued

Reactivities to oligonucleotides in SLE patients compared to controls.

| Antigen | IgM Mean Difference (SLE-HC) | IgM p value | IgM FDR[a] corrected p value | IgM Mean Difference (SLE-HC) | IgG p value | IgG FDR[a] corrected p value |
|---|---|---|---|---|---|---|
| CCATAATTGCAAACGTTCTG | 0.90735 | 0.00043208 | 0.0010001 | 1.8404 | 2.08E-07 | 4.79E-06 |
| $G_{30}$ | 0.85963 | 0.00079088 | 0.0015158 | 1.8957 | 4.27E-07 | 6.55E-06 |
| $G_{20}$ | 0.50976 | 0.019515 | 0.027203 | 1.8547 | 1.49E-06 | 1.71E-05 |
| $G_1T_{16}G_1$ | 0.74997 | 0.00045524 | 0.0010001 | 1.6919 | 3.17E-06 | 2.92E-05 |
| CCATAATTGCAAAGCTTCTG | 0.88558 | 0.00044727 | 0.0010001 | 1.5353 | 6.90E-06 | 4.53E-05 |
| $(TTAGGG)_4$ | 0.75709 | 4.70E-05 | 0.00024047 | 1.3635 | 2.29E-05 | 0.00013154 |
| $G_{17}$ | 0.45068 | 0.036383 | 0.049224 | 1.4023 | 6.98E-05 | 0.00026755 |
| $T_2G_{16}T_2$ | 0.73236 | 0.0046818 | 0.0076916 | 1.6893 | 6.68E-05 | 0.00026755 |
| $A_{20}$ | 0.5841 | 0.0054888 | 0.0087052 | 1.3183 | 0.00018 22 | 0.00055876 |
| $G_{16}T_1$ | 0.7661 | 0.00017384 | 0.00055876 | 1.2069 | 0.00045658 | 0.0010001 |
| $T_{20}$ | 0.60023 | 0.0012888 | 0.0023699 | 1.2048 | 0.00057735 | 0.0012072 |
| $T_1G_{16}$ | 0.78642 | 0.00013 12 | 0.00046425 | 1.0386 | 0.0020908 | 0.0036991 |
| CCATAATTCGAAACGTTCTG | 0.79837 | 0.0099977 | 0.01533 | 0.84121 | 0.010505 | 0.015588 |
| $T_{16}G_2$ | 0.60568 | 0.00075013 | 0.0015003 | 0.67964 | 0.044519 | 0.05851 |
| $G_7$ | 0.60019 | 0.0025561 | 0.0043548 | 0.58484 | 0.084445 | 0.10222 |
| $T_{16}G_1$ | 0.56283 | 0.00020274 | 0.00058287 | 0.58344 | 0.10765 | 0.12697 |
| $G_9$ | 0.76088 | 0.00030908 | 0.00083632 | 0.47427 | 0.18064 | 0.20774 |
| $(GT)_{10}$ | 0.14851 | 0.42349 | 0.45303 | -0.36072 | 0.26665 | 0.29917 |
| $C_{20}$ | 0.63319 | 0.04842 | 0.06187 | -0.38242 | 0.28355 | 0.31056 |
| $(GA)_{10}$ | 0.78848 | 6.58E-05 | 0.00026755 | 0.079545 | 0.71587 | 0.74841 |
| $(CG)_{10}$ | 0.5763 | 0.077347 | 0.096161 | 0.58108 | 0.78416 | 0.80158 |
| $G_{14}$ | 0.44226 | 0.013855 | 0.019917 | -0.04129 | 0.88587 | 0.88587 |

[a]FDR, False discovery rate.

Example 8

Antibody Reactivities to Synthetic Oligonucleotides in SLE Patients Compared to Those of Healthy Subjects FIGS. 7AI, 7AII, 7BI and 7BII list the oligonucleotides with increased IgG (7AI-II) and IgM (7BI-II) binding in 77 SLE patients compared to 83 healthy controls. A broad spectrum of oligonucleotides was found (7AI-II) to be extremely SLE-indicative (p value≤1.87E-08), sensitive (≥0.609), specific (≥0.769) and accurate (≥0.687).

Examples of such oligonucleotide antigens are G1T16 (SEQ ID NO: 42) having a p value 9.49E-15, sensitivity 0.680, specificity 0.822, and accuracy 0.750, CCATAATT-GCAAACGTTCTG (SEQ ID NO: 1) having a p value 2.81E-12, sensitivity 0.657, specificity 0.798, and accuracy 0.725, G1T16G1 (SEQ ID NO: 5) having a p value 1.07E-18, sensitivity 0.767, specificity 0.869, and accuracy 0.819, CCATAATTGCAAAGCTTCTG (SEQ ID NO: 3) having a p value 9.87E-14, sensitivity 0.659, specificity 0.830, and accuracy 0.743, A20 (SEQ ID NO: 22) having a p value 1.87E-08, sensitivity 0.609, specificity 0.769, and accuracy 0.687, T20 (SEQ ID NO: 8) having a p value 8.00E-14, sensitivity 0.663, specificity 0.814, and accuracy 0.738, T16G2 (SEQ ID NO: 28) having a p value 4.81E-15, sensitivity 0.682, specificity 0.856, and accuracy 0.769, and T16G1 (SEQ ID NO: 7) having a p value 2.38E-11, sensitivity 0.656, specificity 0.828, and accuracy 0.741.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of determining the reactivity of antibodies in a sample of a subject suspected of having SLE to at least one oligonucleotide antigen selected from the group consisting of SEQ ID NOs: 42, 5, 28, 1, 3 and 22, comprising:
   i. obtaining a serum, plasma sample or blood sample from the subject;
   ii. providing a plurality of antigens in the form of an antigen probe set, an antigen array, or an antigen chip, said plurality of antigens comprising the at least one oligonucleotide antigen,
   iii. contacting the sample, under conditions such that a specific antigen-antibody complex may be formed, with said at least one oligonucleotide antigen, and
   iv. quantifying the amount of antigen-antibody complex formed for each antigen probe, by a system that allows quantitative measurement of antigen-antibody binding.

* * * * *